(12) United States Patent  
Maher

(10) Patent No.: US 11,987,840 B2
(45) Date of Patent: May 21, 2024

(54) SYSTEMS AND METHODS FOR ASSESSING OF BIOLOGICAL SAMPLES

(71) Applicant: LIFE TECHNOLOGIES CORPORATION, Carlsbad, CA (US)

(72) Inventor: Kevin Maher, Grass Valley, CA (US)

(73) Assignee: Life Technologi s Corporation, Carlsbad, CA (US)

( * ) Notice: Subject to any disclaimer, the term of this patent is extended or adjusted under 35 U.S.C. 154(b) by 0 days.

(21) Appl. No.: 16/234,287

(22) Filed: Dec. 27, 2018

(65) Prior Publication Data

US 2019/0241934 A1    Aug. 8, 2019

Related U.S. Application Data

(63) Continuation of application No. 14/385,766, filed as application No. PCT/US2013/031890 on Mar. 15, 2013, now abandoned.

(Continued)

(51) Int. Cl.
*C12Q 1/686* (2018.01)
*B01L 3/00* (2006.01)
(Continued)

(52) U.S. Cl.
CPC .......... *C12Q 1/686* (2013.01); *B01L 3/50857* (2013.01); *B01L 7/52* (2013.01);
(Continued)

(58) Field of Classification Search
CPC ....... C12Q 1/686; B01L 7/52; B01L 3/50857; B01L 2300/0893; B01L 2300/0636; B01L 2300/0654; B01L 2300/0896
See application file for complete search history.

(56) References Cited

U.S. PATENT DOCUMENTS 6,972,183 B1 * 12/2005 Lafferty ............. C12N 15/1086
435/6.12
8,318,094 B1 * 11/2012 Bayandorian ........ G01N 21/645
422/63

(Continued)

FOREIGN PATENT DOCUMENTS

CN        1861800 A      11/2006
CN     102301005 A      12/2011
(Continued)

OTHER PUBLICATIONS

Hatch et al Lab on a Chip, 2011, 11: 3838-3845. (Year: 2011).*

(Continued)

*Primary Examiner* — Robert T. Crow

(57) ABSTRACT

A system for determining the number of target nucleotide molecules in a sample includes a sample holder, an excitation optical system, an optical sensor, and an emission optical system. The sample holder is configured to receive an article comprising at least 20,000 separate reaction sites. The excitation optical system comprises a light source configured to simultaneously illuminate the at least 20,000 separate reaction sites. The optical sensor comprises a predetermined number of pixels, the predetermined number of pixels being at least 20 times the number of separate reaction sites. The emission optical system comprises a system working distance from the sample holder, wherein the working distance is less than or equal to 60 millimeters.

8 Claims, 12 Drawing Sheets

Related U.S. Application Data

(60) Provisional application No. 61/774,499, filed on Mar. 7, 2013, provisional application No. 61/723,710, filed on Nov. 7, 2012, provisional application No. 61/723,759, filed on Nov. 7, 2012, provisional application No. 61/659,029, filed on Jun. 13, 2012, provisional application No. 61/612,087, filed on Mar. 16, 2012, provisional application No. 61/612,005, filed on Mar. 16, 2012.

(51) Int. Cl.
  *B01L 7/00* (2006.01)
  *G02B 5/00* (2006.01)

(52) U.S. Cl.
  CPC ............... *B01L 2300/0636* (2013.01); *B01L 2300/0654* (2013.01); *B01L 2300/0893* (2013.01); *B01L 2300/0896* (2013.01)

(56) References Cited

U.S. PATENT DOCUMENTS

| | | | |
|---|---|---|---|
| 2002/0164820 A1 | 11/2002 | Brown | |
| 2003/0059094 A1* | 3/2003 | Cattell | C12Q 1/6837 382/128 |
| 2003/0082587 A1 | 5/2003 | Seul et al. | |
| 2004/0033622 A1* | 2/2004 | Delenstarr | G06T 7/0012 436/518 |
| 2005/0232820 A1 | 10/2005 | Reed et al. | |
| 2007/0154938 A1* | 7/2007 | Oshida | G01N 21/6452 356/320 |
| 2009/0225410 A1* | 9/2009 | Fey | G02B 21/16 359/385 |
| 2009/0258383 A1 | 10/2009 | Kovac et al. | |
| 2010/0321696 A1 | 12/2010 | Malik et al. | |
| 2011/0117025 A1* | 5/2011 | Dacosta | A61B 5/01 424/9.6 |
| 2011/0188053 A1 | 8/2011 | Buermann et al. | |
| 2011/0207137 A1 | 8/2011 | Malik et al. | |
| 2011/0220775 A1 | 9/2011 | Triener et al. | |

FOREIGN PATENT DOCUMENTS

| | | |
|---|---|---|
| EP | 1693337 A1 | 8/2006 |
| WO | WO-03018772 A2 | 3/2003 |
| WO | WO-2004074818 A2 | 9/2004 |
| WO | WO-2005028629 A2 | 3/2005 |
| WO | WO-2006053769 A1 | 5/2006 |
| WO | WO-2005028629 A3 | 6/2006 |

OTHER PUBLICATIONS

Andrew C. Hatch, et al., "Lab on a Chip", The Royal Society of Chemistry, 2011, 3838-3845.
Extended European Search Report for Application No. 18172310.7, dated Nov. 23, 2018, 9 pages.
Heyries, et al., "Megapixel Digital PCR", Nature Methods, vol. 8, No. 8, 2011, Pas 649-651.
Margulies et al., "Genome Sequencing in Microfabricated High-Density Picolitre Reactors", Nature, vol. 437, No. 15, 2005, pp. 376-380.
PCT/US2013/031890, "International Preliminary Report on Patentability and Written Opinion dated Sep. 16, 2014", 6 pages.
EP21214013.1, Extended European Search Report, dated Mar. 23, 2022, 9 pages.
PCT/US2013/031890, International Search Report and Written Opinion, dated Jun. 3, 2013, 9 pages.

* cited by examiner

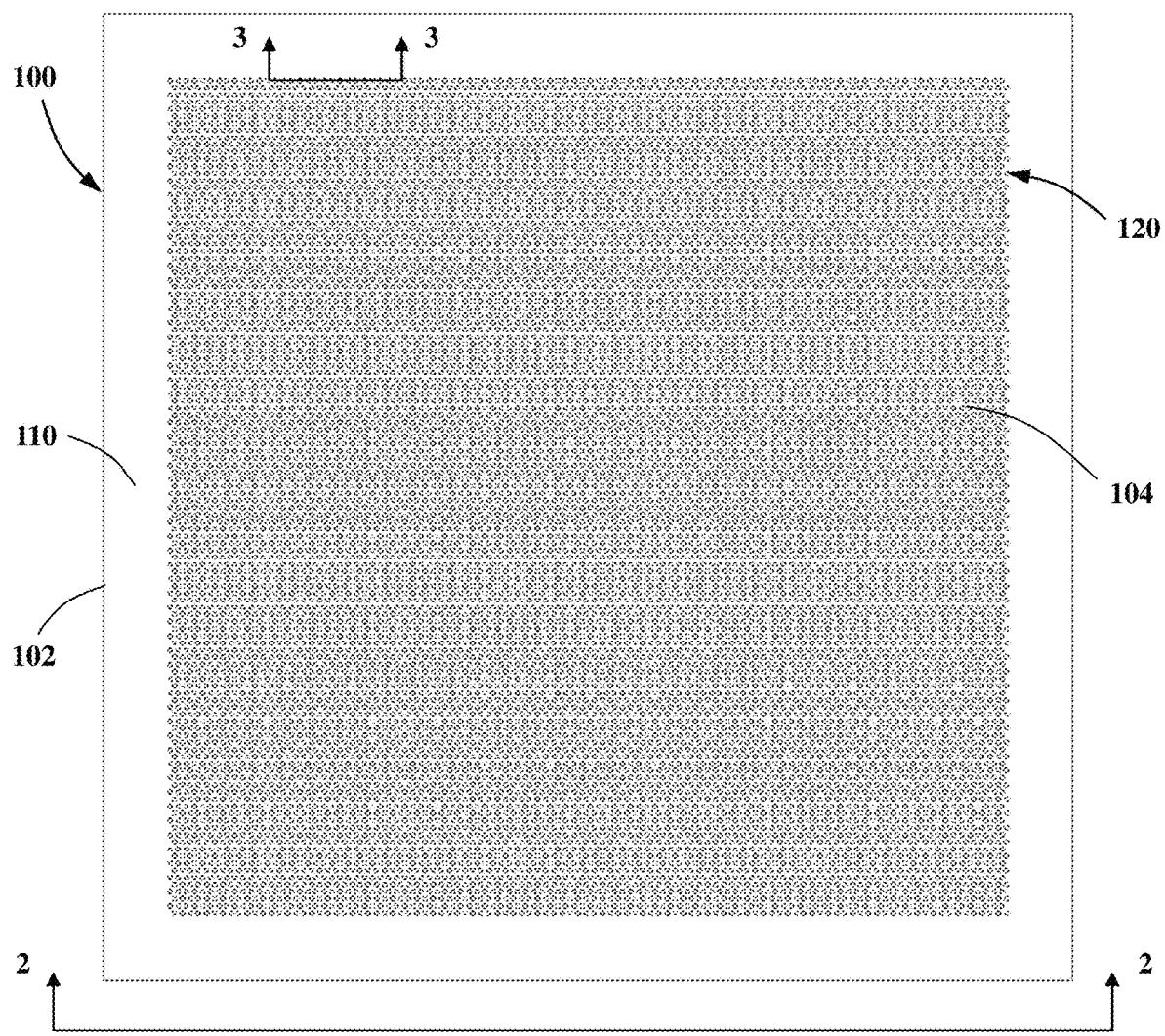
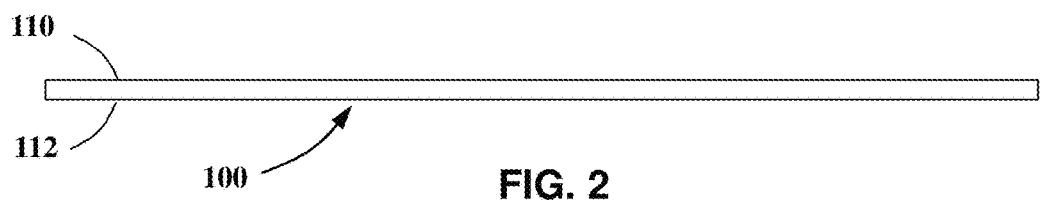
FIG. 1
FIG. 2

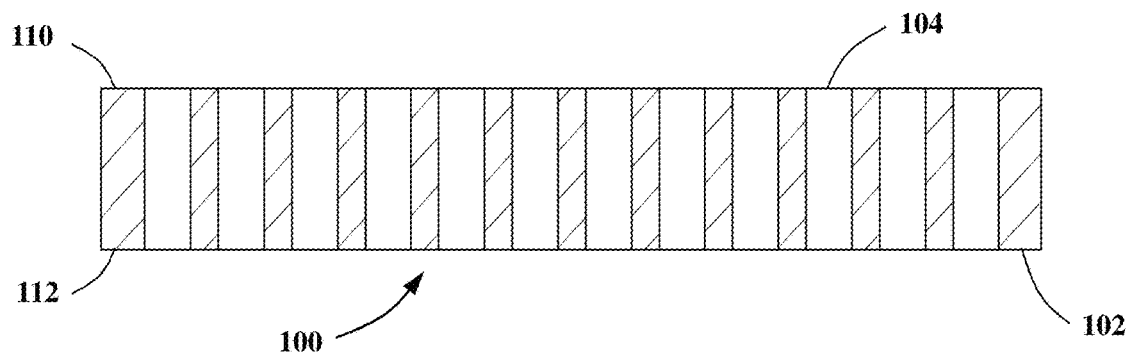
FIG. 3
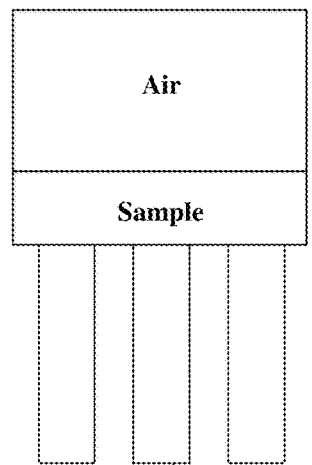
FIG. 4
FIG. 5
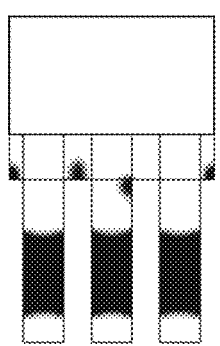
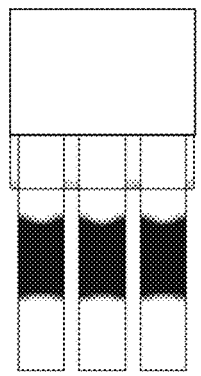

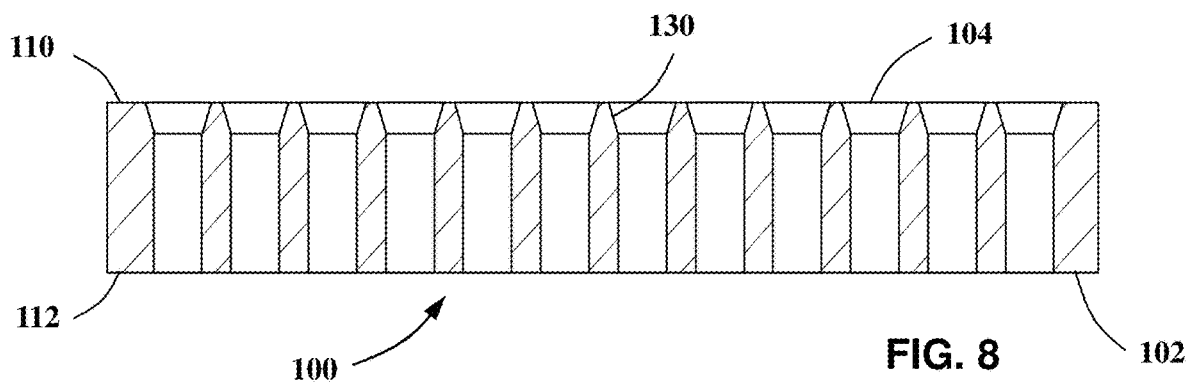
FIG. 8
FIG. 9
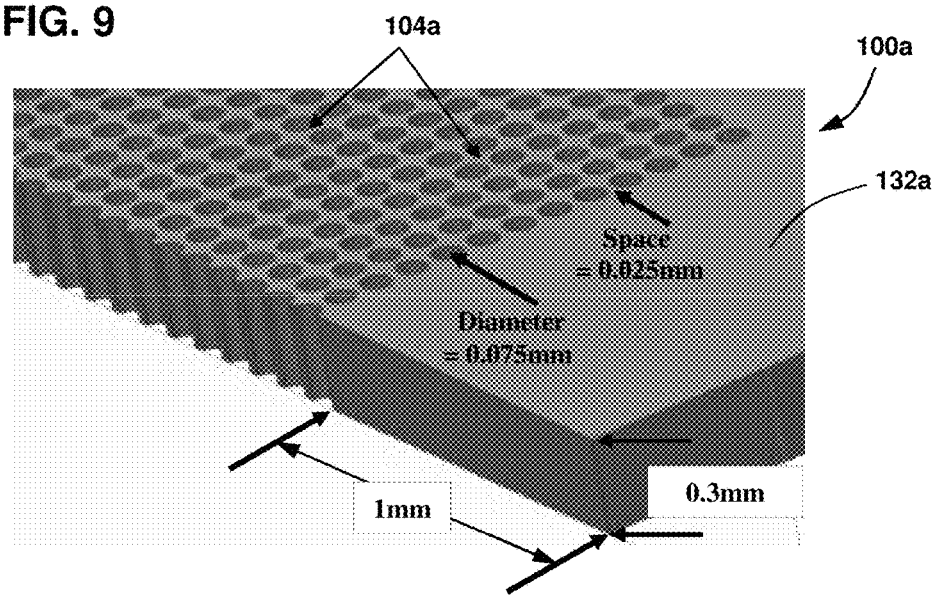
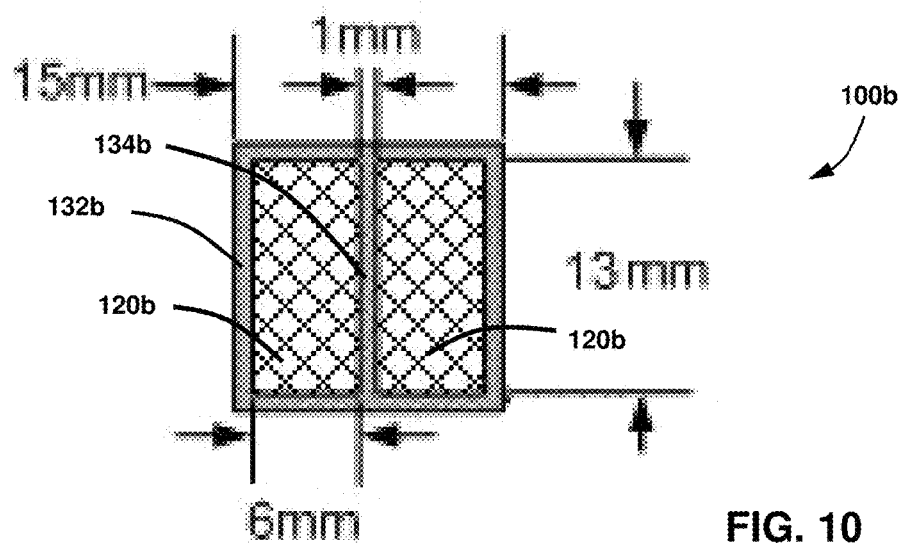
FIG. 10

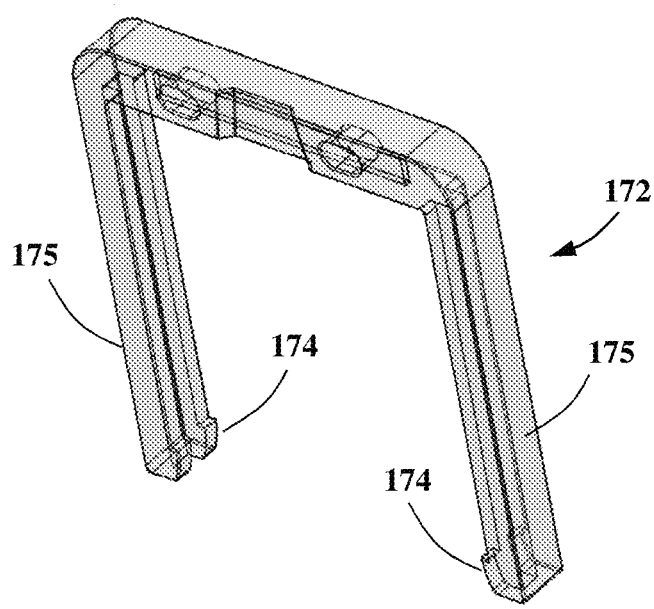
FIG. 15
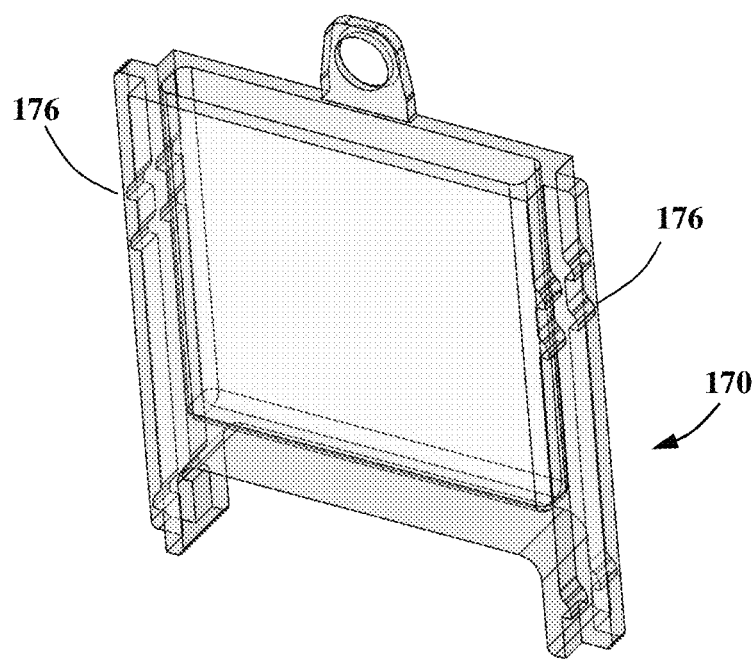

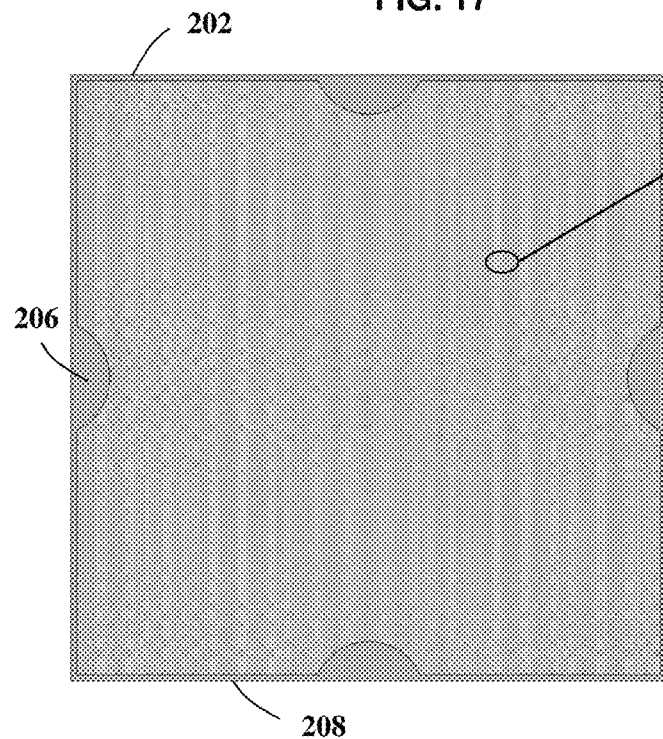
FIG. 17
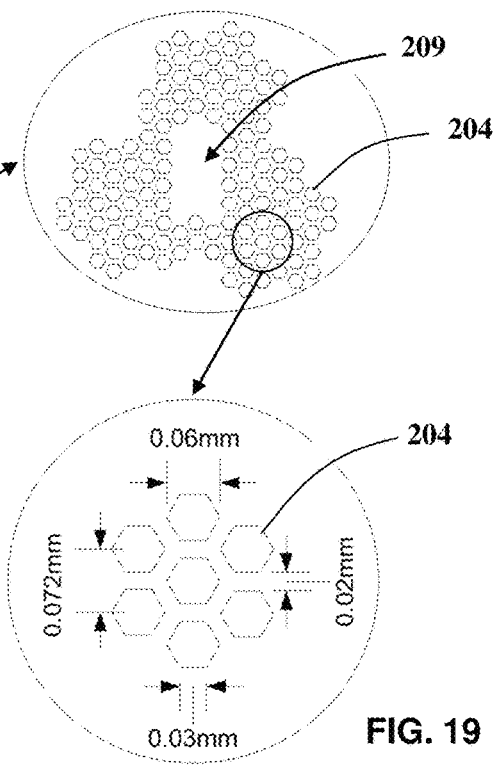
FIG. 18
FIG. 19
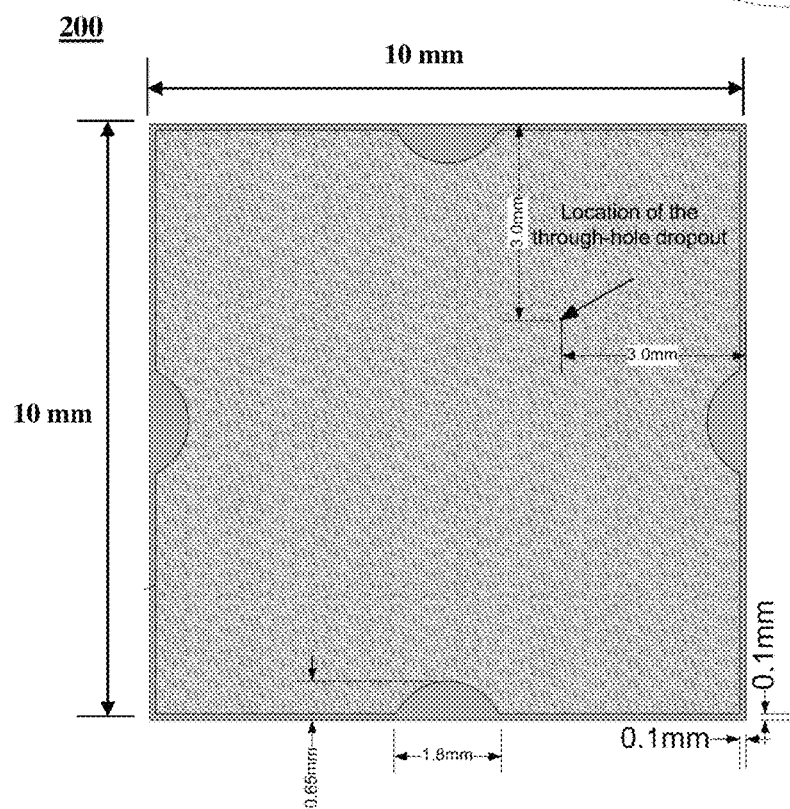
FIG. 20

SYSTEMS AND METHODS FOR ASSESSING OF BIOLOGICAL SAMPLES

BACKGROUND OF THE INVENTION

Field of the Invention

The present invention relates generally to devices, systems, and methods for assessing biological samples, and more specifically to devices, systems, and methods for simultaneously assessing a plurality of biological samples.

Description of the Related Art

Optical systems for biological and biochemical reactions have been used to monitor, measure, and/or analyze such reactions. Such systems are commonly used in sequencing, genotyping, polymerase chain reactions (PCR), and other biochemical reactions to monitor progress and provide quantitative data. For example, an optical excitation beam may be used during real-time PCR (qPCR) processes to illuminate fluorescent DNA-binding dyes or fluorescent probes to produce fluorescent signals indicative of the amount of a target gene or other nucleotide sequence. Increasing demands to provide greater numbers of reactions per test or experiment have resulted in instruments that are able to conduct large numbers of reactions simultaneously.

The increase in the number sample sites in a single test or experiment has led to microtiter plates and other sample formats that provide ever smaller sample volumes. In addition, techniques such as digital PCR (dPCR) have increased the demand for smaller sample volumes that contain either zero or one target nucleotide sequence in a majority of a large number of test samples. There is a need for systems and sample format that will provide reliable data in even high-density sample format with sample sites having volumes on the order of nanoliters or picoliters.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 1 is a top view of a substrate according to an embodiment of the present invention.

FIG. 2 is a side view of the substrate shown in FIG. 1.

FIG. 3 is a cross-sectional view of a portion of the substrate shown in FIG. 1.

FIG. 4 is a schematic representation of model of an embodiment of the present invention FIG. 5 is a schematic representation result using the model shown in FIG. 4

FIG. 8 is a cross-sectional view of a substrate according to an embodiment of the present invention.

FIG. 9 is a perspective view of a portion of a substrate according to an embodiment of the present invention.

FIG. 10 is a top view of a substrate according to an embodiment of the present invention.

FIG. 15 is a perspective view of a carrier according to an embodiment of the present invention.

FIGS. 17 is a front view of an article of manufacture according to an embodiment of the present invention.

FIGS. 18-19 are magnified front views of the article of manufacture shown in FIG. 17.

FIG. 20 is a front view of the article of manufacture shown in FIG. 17 showing various dimensions of the article.

DETAILED DESCRIPTION OF THE DRAWINGS

Figure 6:
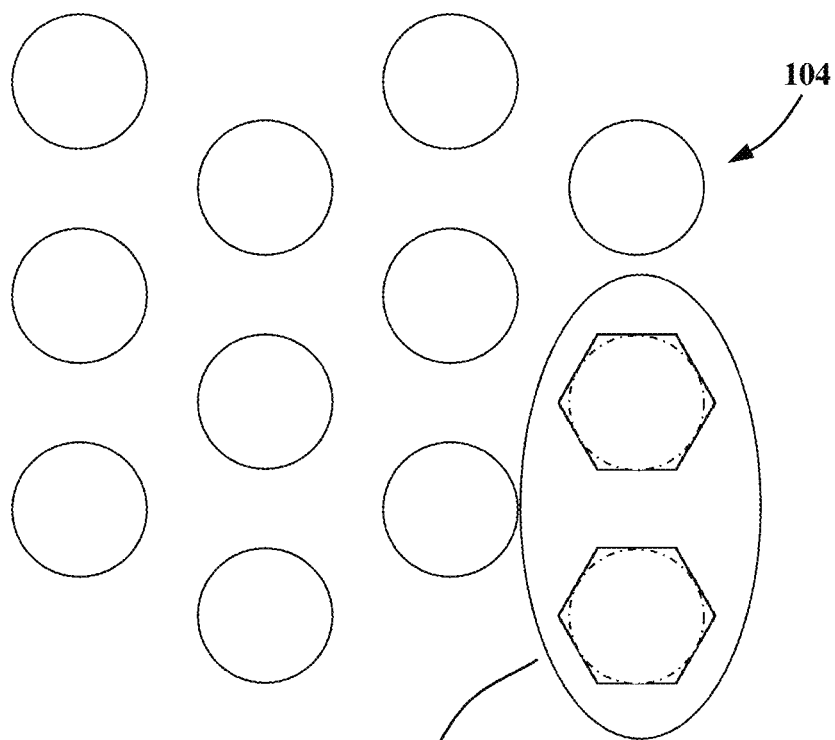
FIG. 6 is a representation of a pattern for distribution of reaction sites according to an embodiment of the present invention

Embodiments of the present invention are generally directed devices, instruments, systems, and methods for monitoring or measuring a biological reactions for a large number of small samples or solutions located at a plurality of reaction regions or reaction sites. Embodiments include the use of polymerase chain reaction (PCR) processes, assays, and protocols. While generally applicable to dPCR (digital PCR) or qPCR (real-time or quantitative PCR) where a large number of samples are being processed, it should be recognized that any suitable PCR method may be used in accordance with various embodiments described herein. Suitable PCR methods include, but are not limited to, which may include, without limitation, allele-specific PCR, asymmetric PCR, ligation-mediated PCR, multiplex PCR, nested PCR, quantitative or real-time PCR (qPCR), cast PCR, genome walking, bridge PCR, digital PCR (dPCR), or the like.

While devices, instruments, systems, and methods according to embodiments of the present invention are generally directed to dPCR and qPCR, the present invention may be applicable to any PCR processes, experiment, assays, or protocols where a large number of samples or solutions test volumes are processed, observed, and/or measured, embodiments of the present invention are particularly well suited for dPCR. In a dPCR assay or experiment according to embodiments of the present invention, a dilute solution containing a relatively small number of at least one target polynucleotide or nucleotide sequence is subdivided into a large number of very small test samples or volumes, such that the vast majority at least some of these samples or volumes contains either one molecule of the target nucleotide sequence or none of the target nucleotide sequence. When the samples are subsequently thermally cycled in a PCR protocol, procedure, assay, process, or experiment, the individual samples containing the one or more molecules of the target nucleotide sequence are greatly amplified and produce a positive, detectable detection signal, while the samples those containing none of the target(s) nucleotide sequence are not amplified and do not produce a no detection signal, or a produce a signal that is below a predetermined threshold or noise level. Using Poisson statistics, the number of target nucleotide sequences in the original solution may be correlated to the number of samples producing a positive detection signal. In some embodiments, the detected signal may be used to determine a number, or number range, of target molecules contained in an individual sample or volume. For example, a detection system may be configured to distinguish between samples containing one target molecule and samples containing two or at least two target molecules. Additionally or alternatively, the detection system may be configured to distinguish between samples containing a number of target molecules that is at or below a predetermined amount and samples containing more than the predetermined amount. In certain embodiments, both qPCR and dPCR processes, assays, or protocols are conducted using a single the same devices, instruments, or systems, and methods.

In various embodiments, the devices, instruments, systems, and methods described herein may be used to detect one or more types of biological components or targets of interest that are contained in an initial sample or solution containing the biological components of interest. These biological components or targets of interest may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule. In various embodiments, such biological components may be used in conjunction with various one or more PCR methods and systems in applications such as fetal diagnostics, multiplex dPCR, viral detection, and quantification standards, genotyping, sequencing assays, experiments, or protocols, sequencing validation, mutation detection, detection of genetically modified organisms, rare allele detection, and/or copy number variation.

According to embodiments of the present invention, one or more samples or solutions containing at least one biological targets of interest may be contained in distributed or divided between a plurality of a small sample volumes or reaction volume sites. The samples or solutions for embodiments of the present invention sample volumes or reaction sites disclosed herein are generally illustrated as being contained in through-holes located in a substrate material; however, where applicable, other forms of sample volumes or reaction sites according to embodiments of the present invention may include be used, including reaction volumes located within wells or indentations formed in a substrate, spots of solution distributed on the surface a substrate, or other types of reaction chambers or formats, such as samples or solutions located within test sites or volumes of a microfluidic system, or within or on small beads or spheres.

In certain embodiments, order to conduct a dPCR protocol, assay, procedure, process, or experiment included distributing or dividing according to embodiments of the present invention, an initial sample or solution may be divided into at least ten thousand reaction sites, at least a hundred thousand reaction sites, at least one million reaction sites, or at least ten million tens of thousands, hundreds of thousands, or even millions of reaction sites, each having reaction site may have a volume of a few nanoliters, about one nanoliter, or that is less than or equal to one nanoliter (e.g., less than or equal to 100 picoliters, less than or equal to 10 picoliters, and/or less than or equal to one picoliter 10's or 100's of picoliters or less), in a way that is simple and cost effective.

When Because the number of target nucleotide sequences contained in the initial sample or solution may be is very small (e.g., less than 1000 target molecules, less than 100 target, less than 10 target molecules, or only one or two target molecules), it may also be important in certain cases in such circumstances that the entire content, or nearly the entire content, of the initial solution be accounted for and contained in or received by one of the sample volumes or reaction sites being processed. For example, where there are only a few target nucleotides present in the initial solution, many some or all of these target nucleotide could potentially be contained in a small residual fluid volume that are that is not successfully loaded into one not located in any of the reaction sites and, therefore, would not be detected, measured, or counted. Thus, efficient transfer of the initial solution helps reduces may aid in reducing the chances or possibility of a miscalculation in the number count of a rare allele or target nucleotide or of failing to detect the presences at all a missing the rare allele or target nucleotide if none of the target molecules are successfully located into one of the designated reaction sites. Accordingly, embodiments of the present invention may be used to efficiently provide a high loading efficiency, where loading efficiency is defined as the volume or mass of an initial sample or solution received within the reaction sites divided by the total volume or mass of the initial sample or solution. and load an initial sample solution into a large number of reaction sites or throughholes in a way that results in all, or essentially all, of the sample or solution being contained in one of a predetermined reaction sites.

Referring to FIGS. 1-3, in certain embodiments of the present invention, an article, device, substrate, slide, or plate 100 comprises a substrate 102 containing a plurality of partitions, through-holes, reaction regions, or reaction sites 104 located in substrate 102. In certain embodiments, article 100 may comprise a chip. Additionally or alternatively, article 100 may comprise a microfluidic device which, for example, may further include a plurality of channels or paths for transferring reagents and/or test solutions to reaction sites 104. In other embodiments, reaction sites 104 comprise a plurality of droplets or beads and article 100 may comprise one or more chambers and/or channels containing some or all of the droplets or beads 104. In such embodiments, droplets or beads 104 may form an emulsion, where some or all of droplets or beads 104 contain one or more target of at least one polynucleotide or nucleotide sequence. Where reaction sites 104 are beads, the beams may optionally include an attached optical signature or label. Droplets or beams 104 may be inspected, monitored, or measured either one at time or in groups containing one or more droplets or beads 104, for example using an imaging system according to embodiments of the present invention.

In the illustrated embodiment, article 100 comprises a first surface 110 and an opposing second surface 112. In the illustrated embodiment, each reaction site 104 extends from an opening 114 in first surface 110 to an opening 116 in second surface 112. While the illustrated embodiment shown in FIG. 3 shows a substrate containing through-holes 104, substrate 102 may additionally or alternatively comprise other types of reaction sites. For example, reaction sites 104 may include reaction volumes located within wells or indentations formed in substrate 102, spots of solution distributed on the surfaces 110 or 112, or other types of reaction chambers or formats, such as samples or solutions located within test sites or volumes of a microfluidic system, or within or on small beads or spheres.

Reaction sites 104 may be configured to provide sufficient surface tension by capillary action to draw in respective amounts of liquid or sample containing a biological components of interest. Article 100 may have a general form or construction as disclosed in any of U.S. Pat. Nos. 6,306,578; 7,332,271; 7,604,983; 7,6825,65; 6,387,331; or 6,893,877, which are herein incorporated by reference in their entirety as if fully set forth herein.

Substrate 102 may be a flat plate or comprise any form suitable for a particular application, assay, or experiment. Substrate 102 may comprise any of the various materials known in the fabrication arts including, but not limited to, a metal, glass, ceramic, silicon, or the like. Additionally or alternatively, substrate 102 may comprise a polymer material such as an acrylic, styrene, polyethylene, polycarbonate, and polypropylene material. Substrate 102 and reaction sites 104 may be formed by one or more of machining, injection molding, hot embossing, laser drilling, photolithography, or the like.

In certain embodiments, surfaces 110, 112 may comprise a hydrophobic material, for example, as described in US Patent Application Publication Numbers 2006/0057209 or 2006/0105453, which are herein incorporated by reference in their entirety as if fully set forth herein. In such embodiments, reaction sites 104 may comprise a hydrophilic material that attracts water or other liquid solutions. An array of such hydrophilic regions may comprise hydrophilic islands on a hydrophobic surface and may be formed on or within substrate 102 using any of various micro-fabrication techniques including, but are not limited to, depositions, plasmas, masking methods, transfer printing, screen printing, spotting, or the like.

It has been discovered that a high reaction site density may be configured to reduce the amount of a solution that is left on surface 110, 112 during a loading process, thus leading to higher loading efficiency or transfer of the initial solution. For example, by reducing ratio of the value of the spacing between adjacent well to the value of the well diameter, the amount of solution left on the surface of a plate may be significantly reduced so that, all, or nearly all, of an initial solution or sample containing biological components of interest is located inside reaction sites 104. In this way the possibility is reduced of missing a rare allele or other target molecule, since it would be less likely that one or more target molecule would remain on the substrate surface instead of being received in one of the designated reaction sites 104.

Referring to FIG. 4, this increase in loading efficiency was demonstrated with a computer model of a hydrophobic surface containing a plurality of hydrophilic reaction sites. The model was used to analyze the distribution of a sample into the plurality of reaction sites as a function of the reaction site pitch (or density) for through-holes having a diameter of 75 micrometers. FIG. 5 demonstrates that as the spacing between reaction sites is decreased (increased density), a greater percentage of an initial liquid sample is captured by the reaction sites, and a lesser amount of residual liquid is left behind on the hydrophobic surface after the loading process. Thus, a higher density of reaction sites 104 of a given cross-sectional dimension provides both an increase in the number of test samples for a given size substrate 102 and decreases or eliminates residual fluid left on surfaces 110, 112 (which may contain a rare allele or other target molecule of interest).

Figure 7:
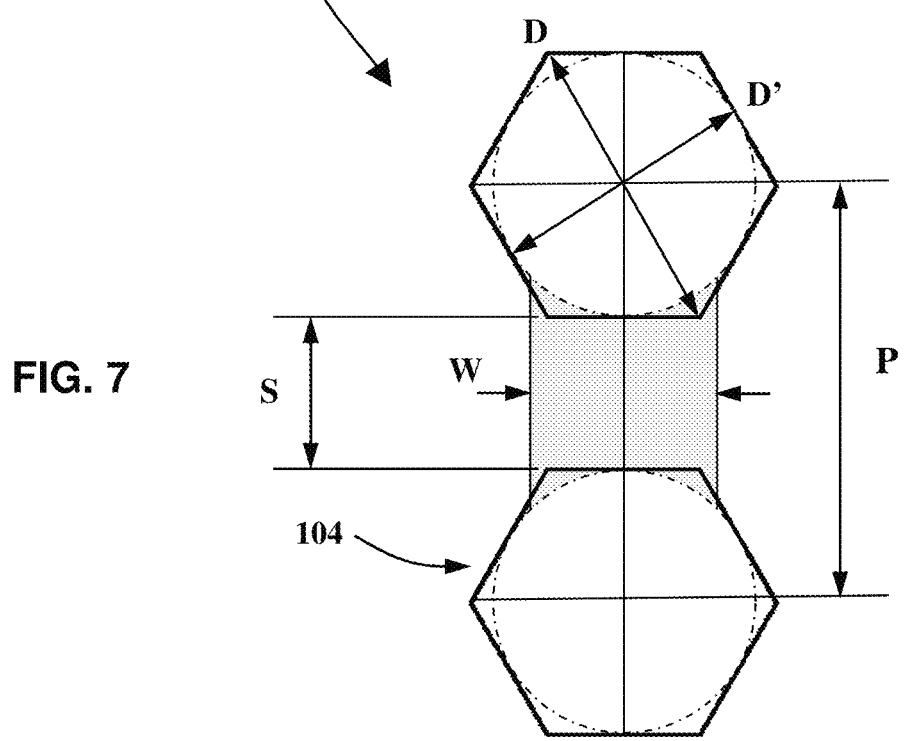
FIG. 7 is a representation of the geometric layout showing a comparison between circular reaction sites and hexagonal reaction sites.

In certain embodiments, a lower bound in the spacing between adjacent reaction sites may exist, for example, due to optical limitations when reaction sites 104 are being imaged by an optical system. For example, the lower bound in spacing between adjacent reaction sites may exist because of limitations in the ability of the optical system to distinctly image adjacent reaction sites. To increase the density of reaction sites 104 in a substrate 102, a close-packed hexagonal matrix pattern may be used, for example, as illustrated in FIGS. 6 and 7.

It has been discovered that reaction sites having a non-circular cross-section may advantageously reduce an average distance or spacing between adjacent reaction sites 104, leading to a reduction in the amount of residual liquid or solution left behind on surfaces 110, 112 after loading of a test solution or sample. Referring to FIGS. 6 and 7, an array of hexagonal reaction sites 104 having a vertex-to-vertex diameter D are arranged in a hexagonal pattern in which the spacing or pitch between adjacent reaction sites is P. In certain embodiments, cross-talk between adjacent reaction sites in an optical system used to measure a fluorescence signal from the reaction sites 104 is a function of a minimum edge distance S between adjacent reaction sites. Thus, the geometry shown in FIG. 7 represents a minimum pitch P between reaction sites that can be used and still maintain the cross-talk between adjacent reaction sites at or below a predetermined value. A dash-lined circle is also shown in FIG. 7 inside each hexagon. This represents a circular reaction site of diameter D' having the same values of pitch P and the same edge spacing S as that of the hexagonal reaction site. The grayed portion in FIG. 7 shows the area between adjacent reaction sites over some width W for both the circular and hexagonal reaction sites. As is clearly seen in FIG. 7, the area between adjacent reaction sites over width W is greater for the circular reaction sites than between the hexagonal reaction sites, when the pitch P and the edge spacing S are the same. The modeling results discussed in regards to FIGS. 4 and 5 show that a smaller area between adjacent reaction sites lead to higher loading efficiency. Thus, based on the results illustrated in FIG. 7, a higher loading efficiency is provided, under the same spacing conditions (P and S), for a hexagonal shaped reaction site than for a circular reaction site.

This result also provides an unexpected advantage for an optical system configured to inspect the reaction sites. Since the minimum edge spacing S in FIG. 7 is the same for both the circular and hexagonal reaction sites, the cross-talk between adjacent reaction sites would be the same or similar for either type of reaction site. However, the cross-sectional area of the hexagonal reaction sites is greater than that of the circular reaction sites, for the same pitch P and edge spacing S. Thus, the image produced by an optical system would have a greater area for hexagonal reaction sites than for circular reaction sites. Accordingly, the larger image produced by the hexagonal reaction site may potentially span a greater number of pixels. A greater number of pixels per reaction site aids in making a more accurate calculation of the signal produced a reaction site. Thus, in addition to providing a higher loading efficiency, the use of hexagonal reaction sites, as shown in FIGS. 6 and 7, may also produce more accurate measurement or calculation of an optical signal or output produce by each reaction site 104 (e.g., measurement or calculation of a fluorescence signal produced in proportion to an amount of a target or dye molecule).

In the illustrated embodiment shown in FIG. 1, article 100 has a square shape and an overall dimension of 15 millimeter by 15 millimeter. Article 100 also has an active area, region, or zone 120 with a dimension of 13 millimeter by 13 millimeter. As used herein, the term "active area", "active region", or "active zone" means a surface area, region, or zone of an article, such as the article 100, over which reaction sites or solution volumes are contained or distributed. In certain embodiments, the active area of article 100 may be increased to 14 millimeter by 14 millimeter or larger, for example on a 15 millimeter by 15 millimeter substrate dimension, in order to increase the total number of reaction sites contained on substrate 102. Article 100 may have other shapes and dimensions. For example, surfaces 110, 112 may be rectangular, triangular, circular, or some other geometric shape. The overall dimensions of article 100 and active area 120 may be smaller or larger than that for the illustrated embodiment in FIG. 1, depending on the particular design parameters for a given system, assay, or experiment.

In the illustrated embodiment of FIG. 1, reaction sites 104 may have a characteristic diameter of 75 micrometer and be distributed over active area 120 with a pitch of 125 micrometers between adjacent reaction sites. In other embodiments, reaction sites 104 have a characteristic diameter of that is less than or equal 75 micrometers, for example, a characteristic diameter that is less than or equal to 60 micrometers or less than or equal to 50 micrometers. In other embodiments, reaction sites 104 have a characteristic diameter that is less than or equal to 20 micrometers, less than or equal to 10 micrometers, less than or equal to 1 micrometer, or less than or equal to 100 nanometers. The pitch between reaction sites may be less than 125 micrometers, for example, less than or equal to 100 micrometers, less than or equal to 30 micrometers, less than or equal to 10 micrometers, or less than or equal to 1 micrometer.

In certain embodiments, substrate 102 has a thickness between surface 110 and surface 112 that is at or about 300 micrometer, so that each reaction site 104 has a volume of about 1.3 nanoliters. Alternatively, the volume of each reaction site 104 may be less than 1.3 nanoliters, for example, by decreasing the diameter of reaction sites 104 and/or the thickness of substrate 102. For example, each reaction site 104 may have a volume that is less than or equal to 1 nanoliter, less than or equal to 100 picoliters, less than or equal to 30 picoliters, or less than or equal to 10 picoliters. In other embodiments, the volume some or all of the reaction site 104 is in a range from 1 nanoliter to 20 nanoliters.

In certain embodiments, the density of reaction sites 104 over surfaces 110, 112 is at least 100 reaction sites per square millimeter. Higher densities are also anticipated. For example, a density of reaction sites 104 over surfaces 110, 112 may be greater than or equal to 150 reaction sites per square millimeter, greater than or equal to 200 reaction sites per square millimeter, greater than or equal to 500 reaction sites per square millimeter, greater than or equal to 1,000 reaction sites per square millimeter, or greater than or equal to 10,000 reaction sites per square millimeter, or greater than or equal to 1,000,000 reaction sites per square millimeter.

Advantageously, all the reaction sites 104 in active area 120 may be simultaneously imaged and analyzed by an optical system. In certain embodiments, active area 120 imaged and analyzed by the optical system comprises at least 12,000 reaction sites 104. In other embodiments, active area 120 imaged and analyzed by the optical system comprises at least 15,000, at least 20,000, at least 30,000, at least 100,000, at least 1,000,000 reaction sites, or at least 10,000,000 reaction sites.

In certain embodiments, reaction sites 104 comprise a first plurality of the reaction sites characterized by a first characteristic diameter, thickness, and/or volume, and a second plurality of the reaction sites characterized by a second characteristic diameter, thickness, and/or volume that is different than that of the corresponding the first characteristic diameter, thickness, or volume. Such variation in reaction site size or dimension may be used, for example, to simultaneously analyze two or more different nucleotide sequences that may have different concentrations. Additionally or alternatively, a variation in reaction site 104 size on a single substrate 102 may be used to increase the dynamic range of a dPCR process, assay, or experiment. For example, article 100 may comprise two or more subarrays of reaction sites 104, where each group is characterized by a diameter or thickness that is different a diameter or thickness of the reaction sites 104 of the other or remaining group(s). Each group may be sized to provide a different dynamic range of number count of a target polynucleotide. The subarrays may be located on different parts of substrate 102 or may be interspersed so that two or more subarrays extend over the entire active area of article 100 or over a common portion of active area of article 100.

In certain embodiments, at least some of the reaction sites 104 are tapered over all or a portion of their walls. For example, referring to FIG. 8, at least some of reaction sites 104 may comprise a chamfer 130 at surface 110. Additionally or alternatively, at least some of reaction sites 104 may comprise a chamfer 130 at surface 112 (not shown). The use of chamfered and/or tapered reaction sites have been found to reduce the average distance or total area between adjacent reaction sites 104, yet without exceeding optical limitations for minimum spacing between solution sites or test samples. As discussed above in relation to FIG. 5, a decrease in the area between adjacent reaction sites 104 may result in a reduction in the amount liquid solution that is left behind on surfaces 110, 112 during a loading process. Thus, a higher sample loading efficiency may be obtained, while still maintaining a larger effective spacing between adjacent solution sites or test samples for the optical system.

In the embodiment shown in FIG. 9, an article, device, array, slide, or plate 100a includes an inactive area, region, or zone 132a that does not contain any reaction sites 104a. The inactive area may be a peripheral zone that surrounds the active zone containing reaction sites 104a. Alternatively, the inactive area may comprise an area that boarders the active zone on one, two, or more sides or zones. In the illustrated embodiment shown in FIG. 9, article 100a has a thickness equal to, or about equal to, 0.3 millimeter and the distance from the edge of the inactive area to the active area is equal to, or about equal to, 1 millimeter; however, other dimensions may be used. In the illustrated embodiment shown in FIG. 9, reaction sites 104a have a diameter that is equal to, or about equal to, 0.075 millimeter and a pitch spacing that is equal to, or about equal to, 0.100 millimeter; however, other dimensions may be used. Where appropriate, features and/or dimensions discussed above in relation to article 100 may be incorporated into article 100a, or vice versa.

Referring to FIG. 10, in certain embodiments, an article, device, array, slide, or plate 100b includes an active area, region, or zone 120b comprising a plurality of reaction sites and an inactive area 132b, wherein inactive area 132b comprises a partition, divider, or separator, 134b that is located between adjacent active areas 120b. As illustrated in FIG. 10, inactive zone 132b may also include a peripheral zone that surrounds active zone 120b. The dimensions shown in FIG. 10 for the various features of article 100b are an example of a particular embodiment and may be different, depending on the requirements of a particular design. For example, partition 134b may have a thickness between active areas 120*b* that less than or equal to 500 micrometers, less than or equal to 1 millimeter, or less than or equal to 2 millimeters or 3 millimeters.

Partition 134*b* may be configured to aid in isolating the reaction sites in one active area, region, or zone from those in a separate active area, region, or zone. Such configurations may be used, for example, to facilitate the loading of a first sample in a first active area and a different second sample in a second active area, where the two areas are separated by partition 134*b*. In certain embodiments, the surface of active areas 120*b* and partition 134*b* are flush with one another on one or both faces of article 100*b*. Additionally or alternatively, at least a portion of partition 134*b* may be raised or offset from active area 120*b* on one or both faces of article 100*b*. In other embodiments, at least a portion of partition 134*b* forms a trough relative to active areas 120*b* for one or both faces of article 100*b*. Where appropriate, features and/or dimensions discussed above in relation to articles 100, 100*a* may be incorporated into article 100*b*, or vice versa.

Figure 11:
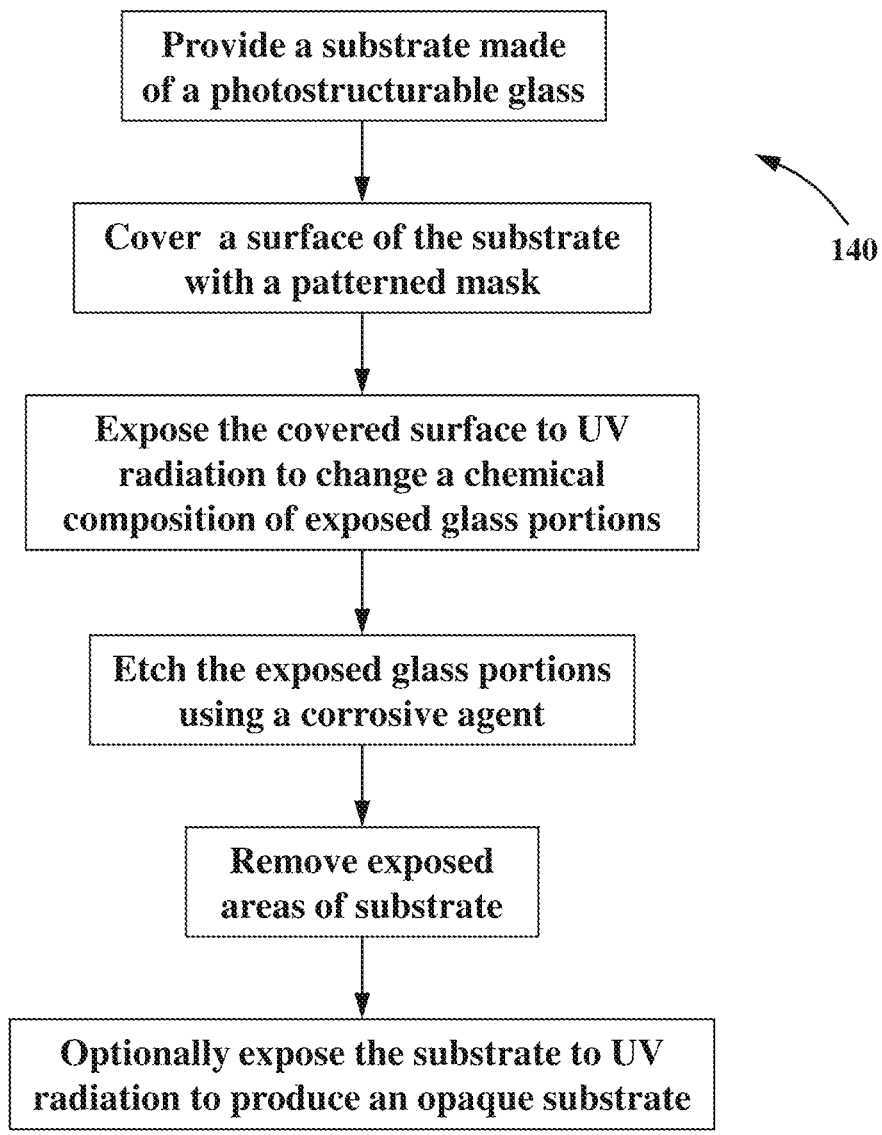
FIG. 11 is a flow chart of a method according to an embodiment of the present invention.

In certain embodiments, substrate 102 comprises a photostructurable material, such as certain glass or ceramic materials. In such embodiments, a method 140 shown in FIG. 11 may be used to fabricate substrate 102. Advantageously, last optional element of method 140 shown in FIG. 11 may be used to provide a substrate 102 that is opaque or nearly opaque, so that light emitted from one reaction site 104 does not enter an adjacent reaction site 104.

Method 140 may be used to provide a substrate 102 having an opacity sufficient prevent any, or nearly any, light emitted in one reaction site 104 from being transmitted into an adjacent reaction site 104. Method 140 may further comprise removing material from substrate 102 by an amount sufficient to reduce thickness between surfaces 110, 112, for example, removing material from substrate 104 by an amount sufficient to reduce the thickness between surfaces 110, 112 by at least 20 percent over an initial thickness or by at least 30 percent or 40 percent over an initial thickness. Method 140 may also include heating substrate 102 to a temperature of at least 500 degrees Celsius during fabrication. In certain embodiments, the patterned mask used in method 140 comprises a quartz plate with chrome pattern. The mask may be removed prior to exposing the at least portion of the substrate to the corrosive agent. The corrosive material used in method 140 may be hydrofluoric acid.

Figure 12:
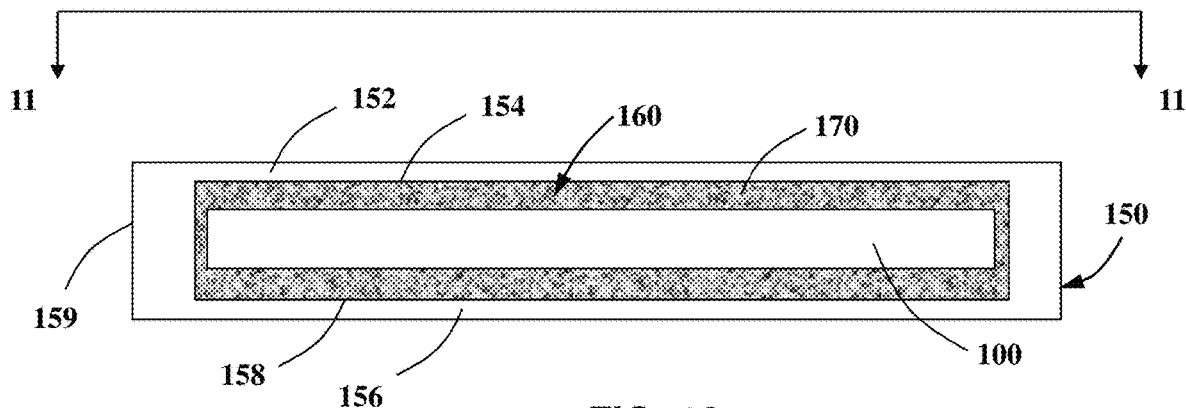
FIG. 12 is a cross-sectional view of a carrier and associated substrate according to an embodiment of the present invention.
Figure 13:
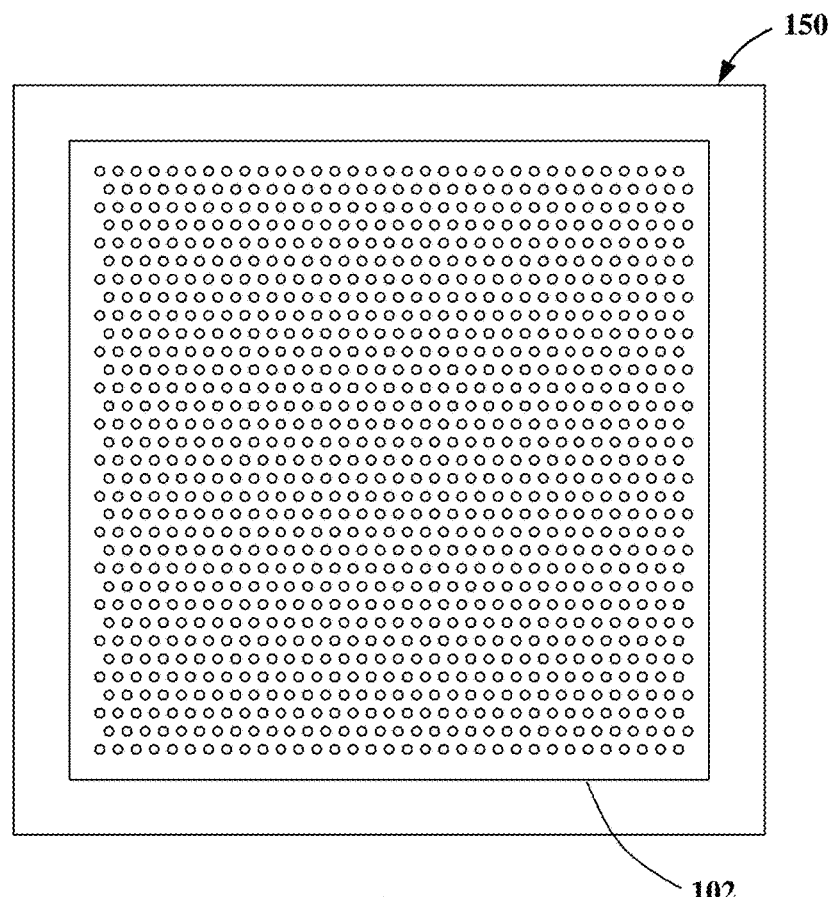
FIG. 13 is a top view of the carrier and substrate shown in FIG. 12.

Referring to FIGS. 12 and 13, in certain embodiments, article 100 is housed within a carrier 150 comprising a first cover 152 having a bottom surface 154 and a second cover 156 having a top surface 158. Carrier 150 may further include one or more side walls 159 configured to maintain a predetermined spacing between the covers 152, 154. The covers 152, 154 and the walls 159 together form a cavity 160 sized to contain article 100. During use, article 100 is disposed within the cavity 160 formed between surfaces 154, 158. The thickness of cavity 160 may be greater than the thickness of article 100 such that there is a gap between article 100 and bottom surface 154 and/or between article 100 and top surface 158. As shown in the illustrated embodiment of FIG. 12, there may also be a gap between one or more side walls 159. Additionally or alternatively, at a portion of article 100 may be attached to one or more of covers 152, 156 and one or more of side walls 159.

Carrier 150 may be made or formed from a metallic material, such as stainless steel, aluminum, copper, silver, or gold, or a semimetal such as graphite. Additionally or alternatively, all or portions of carrier 150 may be made of a non-metallic material including, but are not limited to, glass, acrylics, styrenes, polyethylenes, polycarbonates, and polypropylenes. In certain embodiments, at least one of the covers 152, 156 comprises a suitably transparent material for providing a window configured to allow optical access to and/or from reaction sites 104. Additionally or alternatively, the entire carrier 150 may be made of one or more transparent or nearly transparent materials.

Figure 14:
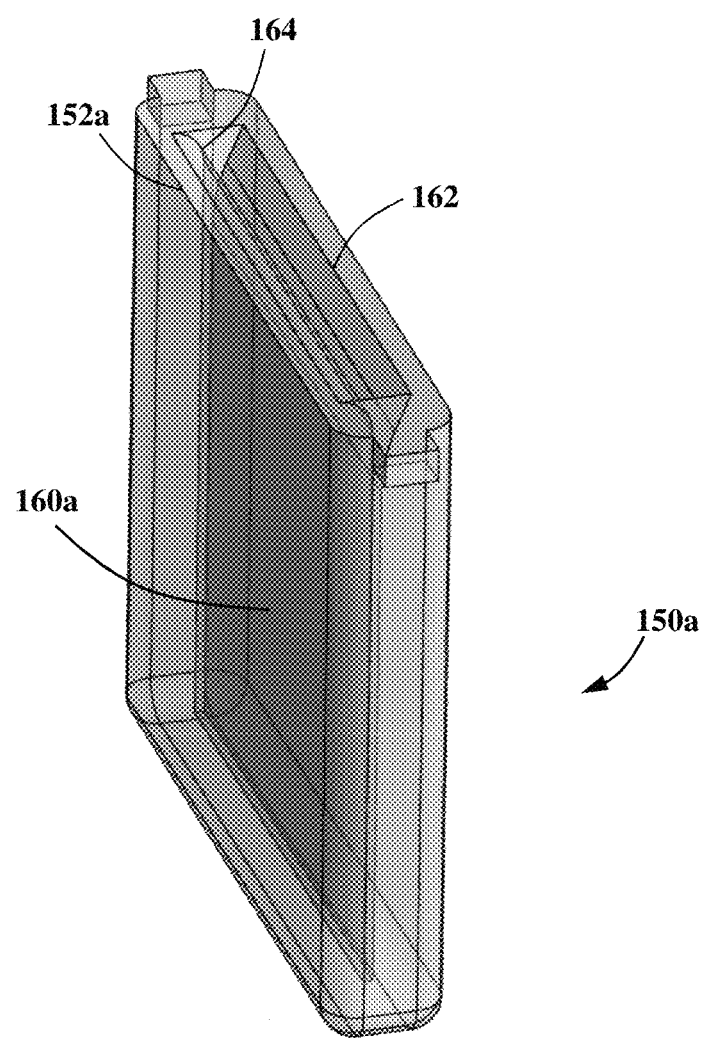
FIG. 14 is a perspective view of a carrier according to an embodiment of the present invention.

Referring to FIG. 14, in certain embodiments, a carrier 150*a* comprises an aperture, port, or opening 162 that may be disposed generally perpendicular to a cover or optical access window 152*a* and sized to allow passage of article 100 into carrier 150*a*. Carrier 150*a* may further comprise a wiper or blade 164 disposed along at least one long edge of opening 162. Blade 164 may be configured to contact or engage at least one of surfaces 110, 112 of article 100 when article 100 is loaded into carrier 150*a*. Carrier 150*a* may further comprise a film or membrane (not shown) disposed over all or a portion of opening 162 that helps to seal cavity 160*a* and is pierced when article 100 is loaded into carrier 150*a*. In certain embodiments, the membrane and blade 164 form a single piece.

In certain embodiments, blade 164 is configured to aid in distributing sample fluid into some or all of reaction sites 104 as article 100 is inserted into carrier 150 through opening 162. For example, blade 164 may be configured to contact one or both surfaces 110, 112 during loading of article 100, so that liquid does not pass blade 164, but is instead pushed, and/or pulled by capillary forces, into reaction sites 104 as surface 110, 112 moves past blade 164. Additionally or alternatively, blade 164 may be configured to cover one or both surfaces 110, 112 of article 100 with a liquid, gel, or the like, for example to reduce or eliminate contamination and/or evaporation of sample fluid contained inside reaction sites 104.

Where appropriate, carrier 150*a* may incorporate any of the structures or features discussed above in relation to carrier 150, or vice versa.

Referring to FIG. 15, in certain embodiments, a carrier 150*b* comprises a body 170, which may include some or all of the structures and features of carrier 150 and/or carrier 150*a*. Carrier 150*b* further comprises a loader or insertion tool 172 for holding article 100, for aiding in loading article 100 into a body 170, and/or for loading a test solution into reaction sites 104. Tool 172 may have a U-shaped body, wherein article 100 is held inside the "U" prior to loading into body 170. Tool 172 may include tabs 174 on opposite arms 175 that are configured to engage or press into corresponding tabs or similar structure 176 of body 170.

Portions of cavity 160 between article 100 and surfaces 154, 158 may be filled with an immiscible fluid 170 (e.g., a liquid or a gel material) that does not mix with test solution contained in reaction sites 104 and configured to prevent or reduce evaporation of the test solution contained from reaction sites 104. One suitable fluid 170 for some applications is Fluorinert, sold commercially by 3M Company. However, in certain embodiments, Fluorinert may be problematic for certain PCR applications due to its propensity to readily take up air that may be later released during PCR cycling, resulting in the formation of unwanted air bubbles.

Alternatively, in certain embodiments, it has been discovered that polydimethylsiloxane (PDMS) may be used in cavity 160 if the PDMS is not fully cross-linked. In such embodiment, PDMS has been found to have several characteristics that make it suitable for use with PCR, including low auto-fluorescing, thermal stability at PCR temperatures, and being non-inhibiting to polymerization processes. In addition, PDMS may contain an aqueous sample but be gas permeable to water vapor. A typical siloxane to cross linking agent used for general applications outside embodiments of the present invention is at a ratio of 10:1 (10 percent cross-linker) by weight.

It has been discovered that by under cross-linking a PDMS material, the resulting material can function as a suitable encapsulant for reducing evaporation, while also retaining the favorable attributes discussed above and associated with the fully cross linked material. More specifically, an under cross-linked PDMS material may be formed by using less than 10 percent of the cross-linker by weight. For example, a cross link level of less than or equal to 1% by weight has been shown to meet design requirements for certain PCR applications, such as for certain dPCR applications. Multiple dPCR responses have been demonstrated using a flat plate 100 that is encapsulated with an amount of cross-linker that is less than or equal to 0.8 percent by weight. Further, due to the higher viscosity of the under cross-linked PDMS material, as compared to Fluorinert, a PDMS encapsulant may also lend itself packaging requirements and customer workflow solutions.

Figure 16:
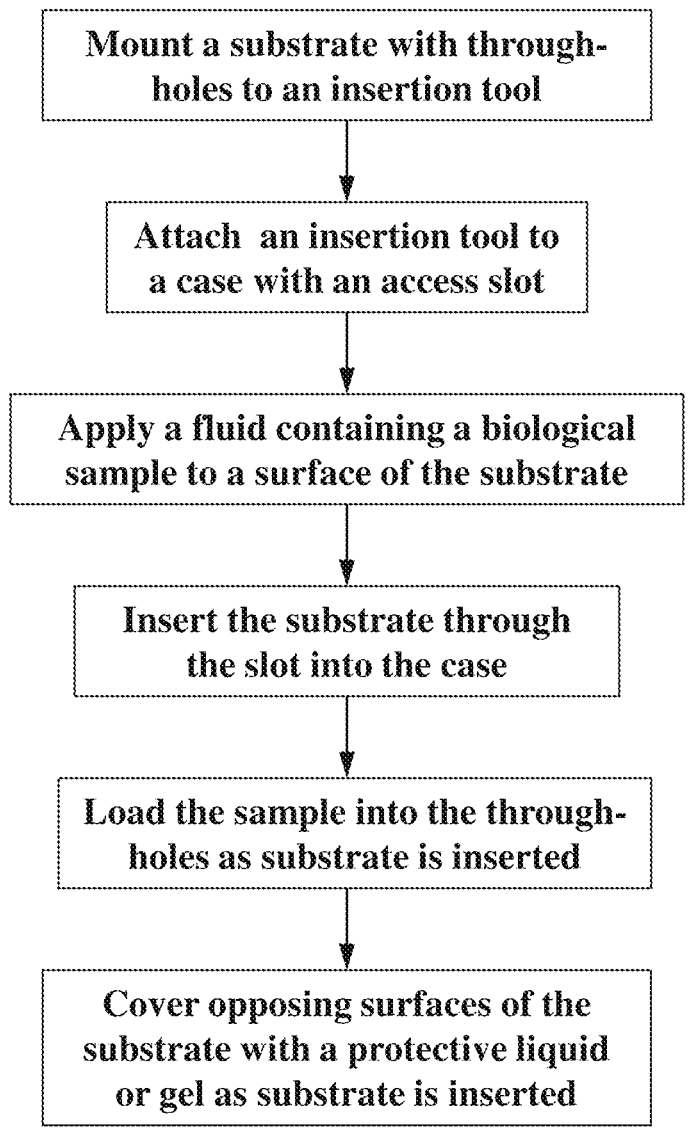
FIG. 16 is a flow chart of a method according to an embodiment of the present invention.

Referring to FIG. 16, a method 200 of preparing a plurality of biological samples comprises providing a substrate of an article such as article 100, 100a, or 100b. Method 200 further comprises providing a carrier such as carrier 150, 150a, or 150b, and providing an insertion tool such as insertion tool 172, the insertion tool comprising a U-shaped body that includes a pair of arms configured to slideably engage the carrier. Method 200 also includes mounting or attaching the substrate to the insertion tool and the insertion tool to the carrier. In certain embodiments, the substrate is mounted or attached to the insertion tool, then the insertion tool and substrate together are mounted to the carrier. In other embodiments, the insertion tool is mounted to the carrier without the substrate, then the substrate is later mounted to the insertion tool and/or the carrier.

Once the substrate is mounted or attached, method 200 includes sliding the insertion tool along the carrier by an amount sufficient to locate the substrate inside the carrier, for example, by inserting the substrate through an opening and/or membrane of the carrier. Using the method 200, a solution or sample may be applied to a face of the substrate in such a way that the solution is deposited or drawn into reaction sites or through-holes in the substrate as the substrate is inserted into the carrier. In addition, one of both surfaces of the substrate may be covered with a liquid or gel, for example, in order to protect the solution from contaminants and/or evaporation.

In certain embodiments, at least 99 percent of the liquid sample is received by at least some of reaction sites. In other embodiments, at least 99.5 percent or 99.9 percent of the liquid sample is received by at least some of reaction sites. In certain embodiments, the total volume of reaction sites 104 is selected to be greater than the volume of the liquid sample to be loaded into reaction sites 104. This has been found to increase the loading efficiency, which can be critical in certain circumstances, as discussed above. In certain embodiments, the ratio of the liquid volume sample to the total volume of all reaction sites 104 is less than or equal to 95 percent. In other embodiments, the ratio of the liquid volume sample to the total volume of all reaction sites 104 is less than or equal to 90 percent, less than or equal to 80 percent, or less than or equal to 70 percent. In certain embodiments, the value of this ratio depends on the percent of the total volume of each reaction site that is filled with liquid after loading. For example, if only 90 percent of each reaction site 104 contains liquid sample after loading, then the ratio of the liquid volume sample to the total volume of all reaction sites 104 may be less than or equal to 90 percent, less than or equal to 80 percent, less than or equal to 70 percent, or less than or equal to 60 percent.

Referring to FIGS. 17-20, in certain embodiments an article, device, array, slide, or plate 200 comprises a substrate 202 containing a plurality of through-holes or reaction sites 204 located in substrate 102. Substrate 202 comprises a first surface and an opposing second surface. In the illustrated embodiment, each reaction site 204 extends from an opening in the first surface to an opening in the second surface. As illustrated in FIGS. 18 and 19, reaction sites 204 may have a hexagonal shape and/or be arranged in a close-packed hexagonal matrix pattern. Alternatively, some or all of reaction sites 204 may have a shape, diameter, density, thickness, pitch spacing, or the like discussed above in relation to reaction sites 104. Article 200 further comprises one or more tabbed, cutout, or blank regions 206 in which no reaction sites 204 are present. As discussed below, blank regions 206 may be located in support regions for article 200. In the illustrated embodiment, blank regions define four semi-circular shape; however, other shapes and sizes are anticipated. In addition, article 200 may include a blank perimeter 208 in which no reaction sites are located.

In certain embodiments, substrate 202 comprise silicon, which may be configured to provide an even temperature distribution across article 200 during use. Alternatively, substrate 202 comprises a glass material, such as a photo-structured glass ceramic, or a metal, such as aluminum, copper, or stainless steel.

Referring to FIG. 18, reaction sites 204 may be arranged so as to define one or more dropout regions 209 located within the array of reaction sites 204. In some embodiments, drop regions 209 have a dimension suitable of viewing with an unaided eye (e.g., visible to the unaided eye without the use of a magnifying device). In the illustrated embodiment, article 200 comprises one dropout region 204 located in a first quadrant of article 200; however, multiple dropout regions on a single article 200 may be incorporated. One or more dropout regions 209 may define an overall shape that is longer along one axis than along an orthogonal axis, as illustrated in FIG. 19. Thus, the use of the single elongated dropout region 209 shown if FIG. 18 that is located away from a center of article 200 allows a uses to determine the orientation of article 200 (e.g., to determine which side is the front and back, and determine the proper orientation about an axis perpendicular to the page of FIGS. 17-19). Dropout regions 209 may also be configured to provide a reference signal, for example, a reference optical signal used during optical inspection of reaction sites 204.

In certain embodiments, a plurality of dropout regions 209 may be configured provide information about the article 200 based on, for example, the dropout shape(s), number of dropout regions 209, and/or the relative position of one dropout region 209 to another dropout region 209. For example, the number of dropout regions on a particular article 200 may be used to determined the diameter of reaction sites 204 and/or the distance between dropout regions 209, or the geometry of the dropout regions 209 to one another, may be used to determine the number of reaction sites 204 or the pitch between reaction sites 204. Many other combinations of dropout regions size, shape, and distribution are anticipated.

Referring to FIG. 20, article 200 may have an overall dimension of or about 10 mm by 10 mm. FIG. 20 also shows the value of other dimensions relevant to the particular embodiment shown in FIG. 20.

Figure 21:
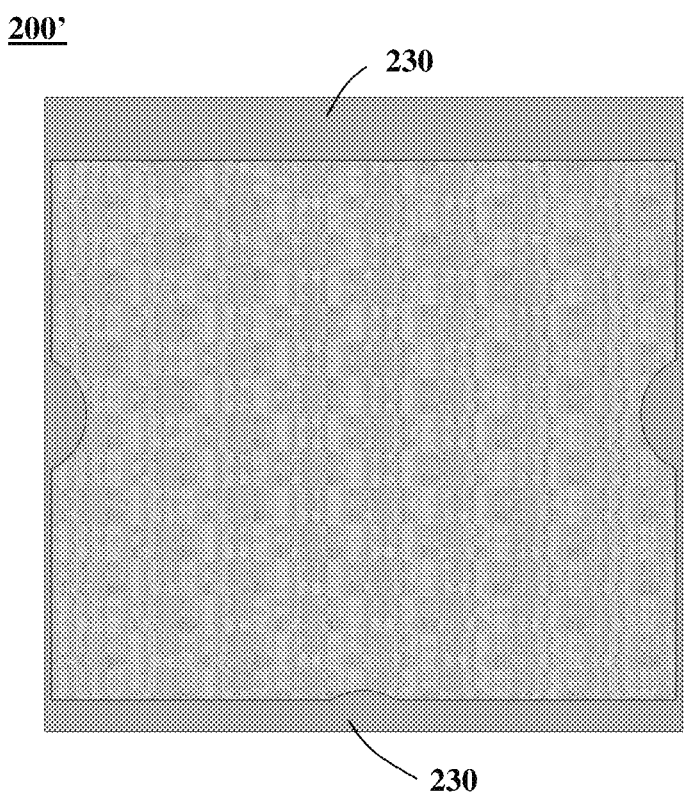
FIG. 21 is a front view of an article of manufacture according to an embodiment of the present invention.
Figure 22:
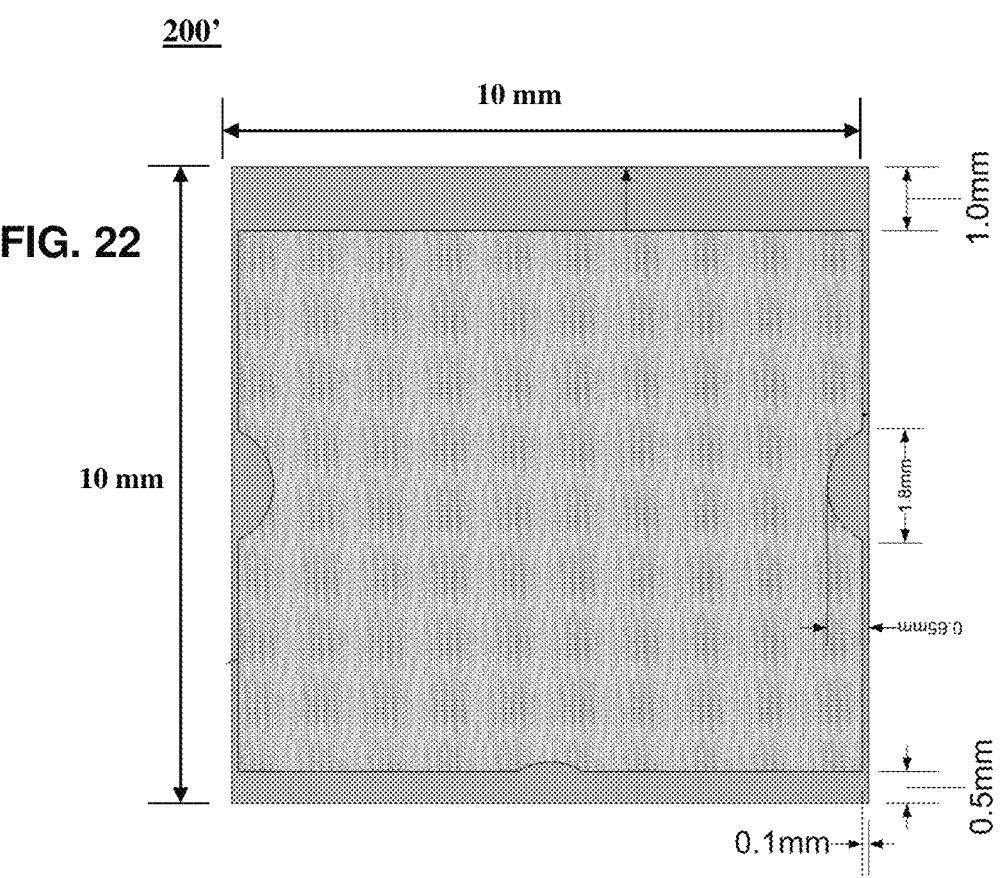
FIG. 22 is a front views of the article of manufacture shown in FIG. 21 showing various dimensions of the article.

Referring to FIGS. 21 and 22, an article 200' may be configured similar to article 200 in FIG. 17, expect that article 200' also includes one or more landing regions 230 that may be size to provide more favorable loading properties. Thus, one or more edges of article 200' have wider zones without reaction sites 204 than other edges of article 200'.

Article 200 may incorporate, where appropriate, various of the elements and/or features discussed in relation to article 100, or vice versa. In addition, article 200 may be used in carrier 150 or other carriers according to embodiments of the current invention. Article 200 may be used in conjunction with system 400 or method 140 in ways similar to those in which article 100 has been disclose herein, as well as in or with other systems and methods disclosed herein in relation to article 100.

Various methods and devices may be used to provide detection of one or more biological components of interest that are contained in reaction sites 104. For example, various fluorescent dyes or markers may be incorporated into solutions containing one or more biological components of interest, which may then be detected using an optical system to determine the presence or amount of the one or more biological components. In other embodiments, the presence of ions (positive or negative) may be detected and/or changes in pH, voltage, or current may be used to determine the presence or amount of one or more biological components of interest.

Figure 23:
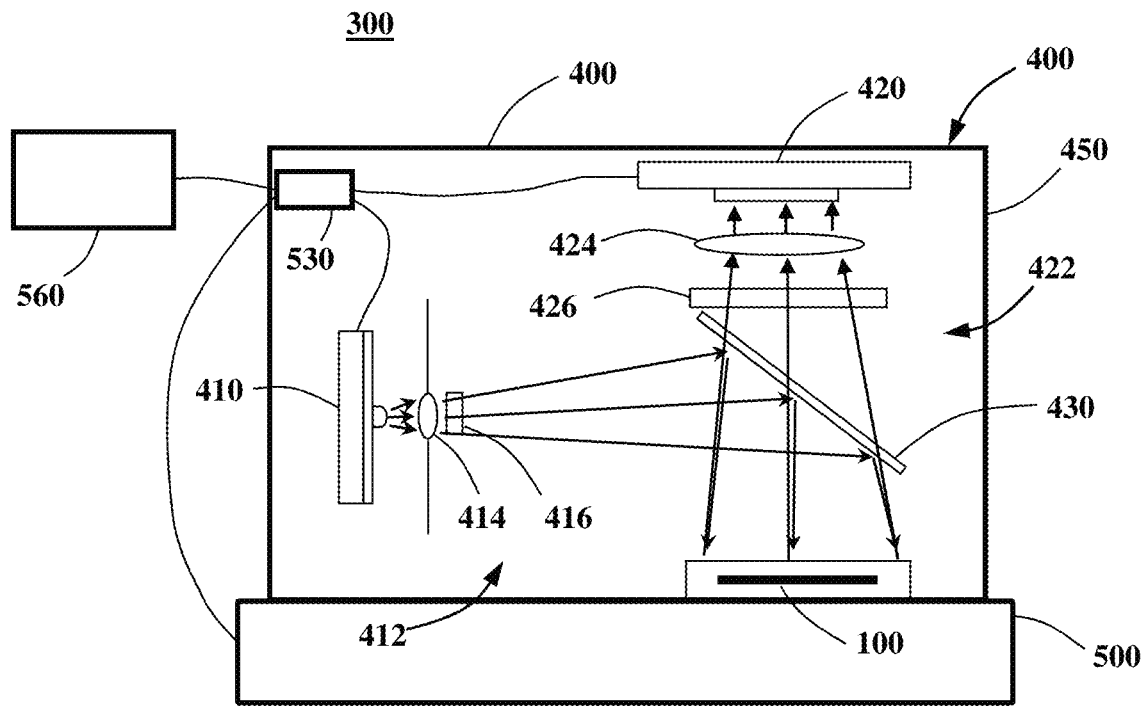
FIG. 23 is a schematic representation of a system according to an embodiment of the present invention.

Referring to FIG. 23, a system 300 may be used to optically view, inspect, or measure one or more samples or solutions containing biological components of interest that are located in reaction sites 104 of article 100. System 300 comprises an optical head or system 400 configured to read or monitor some or all of the reaction sites 104 of article 100, article 200, or the like. In certain embodiments, system 100 may further include one or more of a thermal control system 500, an integrated controller, computer, computational system, or processor 530 located on or within the optical head or system 400 and/or thermal control system 500, and/or an external controller, computer, or processor 560 located external to optical head or system 400 and thermal control system 500.

Either or both computers 530, 560 may include electronic memory storage containing instructions, routines, algorithms, test and/or configuration parameter, test or experimental data, or the like. Either or both computers 530, 560 may be configured, for example, to operate various components of optical system 400 or to obtain and/or process data provided by system 300. For example, either or both computers 530, 560 may be used to obtain and/or process optical data provided by one or more photodetectors of optical system 400. In certain embodiments, integrated computer 530 may communicate with external computer 560 and/or transmit data to external computer 560 for further processing, for example, using a hardwire connection, a local area network, an internet connection, cloud computing system, or the like. External computer 560 may be physical computer, such as a desktop computer, laptop computer, notepad computer, tablet computer, or the like. Additionally or alternatively, either or both computers 530, 560 may comprise a virtual device or system such as a cloud computing or storage system. Data may be transferred or shared between computers 530, 560 via a wireless connection within a local area network, a cloud storage or computing system, or the like. Additionally or alternatively, data from system 300 (e.g., from optical system 400 and/or thermal controller 500) may be transferred to an external memory storage device, for example, an external hard drive, a USB memory module, a cloud storage system, or the like. System 300 may include both computers 530, 560. Alternatively, system 300 may include only one of either computer 530 or computer 560. In such embodiments, data from computer 530 or computer 560 may be stored, transferred, or processed via a hardwire connection, a local area network, an internet connection, cloud computing system, or the like.

In certain embodiments, system 300 does not include thermal control system 500 within a common housing or instrument. For example, optical system 400 may be configured to receive a chip or plate such as article 100 or 200 that was processed in a separate thermal control system, such as a PCR thermal cycler. Optical system 400 may then be used to perform an endpoint PCR or dPCR experiment or assay. In certain embodiments, the external thermal controller is configured to process a plurality of chips or plates, for example, in the form of article 100, 200, or the like. In such embodiments, optical system 400 is configured to receive one or more of the plurality of chips or plates in order to perform a dPCR experiment or assay. A computer system such as computer 530 and/or computer 560 may be used to perform a dPCR analysis based on data from the plurality of chips or plates. In such embodiments, the computer system may be configured to pool data from the chips or plate, for example, to increase the effective sample size of a dPCR experiment or assay to create a "virtual chip". For example, a plurality of articles 100, 200 comprising at least 15,000 or at least 20,000 through-holes or partitions for containing samples may be processed in a separate PCR thermal cycler (either together, in groups, or separately), then examined using optical system 400, either one chip or plate at a time or in groups thereof, to provide pooled dPCR data or a virtual chip comprising at least 100,000 samples, at least 1,000,000 samples, or at least 10,000,000 samples.

In certain embodiments, optical system 400 comprises a light source 410 and an associated excitation optic system 412 configured to illuminate at least some of samples contained in the reaction sites of article 100 or 200. Excitation optical system 412 may include one or more lenses 414 and/or one or more filters 416 for conditioning light directed to the samples. Optical system 400 may further comprise a photodetector or optical sensor 420 and an associated emission optical system or imaging system 422 configured to receive radiation emitted by at least some of the reaction sites 104, 204 and to direct this radiation onto optical sensor 420, for example, by forming an image of article 100 or 200 or reaction sites 104 or 204 at or near optical sensor 420. Radiation received by the emission optical system may comprise fluorescent emissions produced within reaction sites 104, 204 in response to one or more excitation beams produced by light source 410. Additionally or alternatively, radiation received by the emission optical system may be other types of luminescence produce within reaction sites 104, 204, for example, bioluminescence, chemiluminescence, phosphorescence, or the like. For example, when system 300 is configured to perform a qPCR and/or a dPCR procedure, assay, or process, reaction sites 104, 204 may contain one or more fluorescent dyes or markers that provide a fluorescent signal that varies according to an amount of a target nucleotide sequence or molecule contained in various or all of the reaction sites of article 100, 200.

Emission optical system 422 may include a lens or lens system 424 and/or one or more filters 426 for conditioning light directed to the samples. In the illustrated embodiment shown in FIG. 23, excitation/emission optical systems 412, 422 both comprise one or more common optical elements. For example, excitation/emission optical systems 412, 422 may both comprise a beamsplitter 430 that reflects excitation light and transmits emission light from the samples to optical sensor 420. In certain embodiments, excitation/emission optical systems 412, 422 both comprise a field lens (not shown) disposed between beamsplitter 430 and article 100, 200, which may be used improve optical performance, for example, by providing even illumination and/or emission of light to and from the reaction sites 104, 204. In certain embodiments, for example where even illumination or emission (for example as provided by a telecentric optical system) is less critical (e.g., some dPCR applications), the common field lens may be omitted, as shown in the illustrated embodiment of FIG. 23. Omission of the field lens may help to reduce the size and complexity of optical system 400. Exemplary embodiments of excitation and emission optical systems are discussed in U.S. Pat. Nos. 6,818,437; 7,498,164; 7,387,891; 7,635,588; or 7,410,793, which publications are herein incorporated by reference in their entirety.

Lens 424 may comprise a single lens or simple lens, for example, a plano-convex lens, a plano-concave lens, a bi-convex lens, a bi-concave lens, a meniscus lens, or the like. Additionally or alternatively, lens 424 may comprise a compound lens and/or lens system, for example, an achromatic lens, a multi-element lens, a camera lens, a lenslet array, or the like. In certain embodiments, lens 424 may comprise one or more reflective optical elements or diffractive optical elements, such as a diffractive lens, a diffractive grating, a holographic optical element, or the like.

Optical sensor 420 may comprise one or more photodiodes, photomultiplier tubes (PMTs), or the like. Such photodetectors may be used, for example, where optical system 400 is configured to scan individual reaction sites 104, 204 or subsets of reaction sites 104, 204. In other embodiments, optical sensor 420 may comprise one or segmented detector arrays, for example, one or more CCD (charge coupled device) or CMOS (complementary metal-oxide semiconductor) arrays. Segmented detector arrays may be advantageously used where all or large groups of reaction sites 104, 204 are simultaneously imaged or inspected. In order to provide a plurality of pixels per each reaction site, optical sensor 420 may comprise at least 4,000,000 pixel or more than 10,000,000 pixels. In embodiments where optical sensor 420 comprises a segmented detector and/or comprises one or more common optical elements, optical system 400 may be configured so that a plurality of the reaction sites (e.g., reaction sites 104, 204, or the like) are each imaged onto a single pixel or photo-element, or a group of pixels or photo-elements, of optical sensor 420. For embodiments where optical sensor 420 comprises a segmented detector, imaging optical system 422 may be configured to form an image of individual reaction regions of article 100, 200, or the like. Additionally or alternatively, emission optical system 422 may be configured to from an image comprising a plurality of the reaction regions of article 100, 200, or the like Any or all of the components or elements of optical system 400 may be mounted to one or more common frames (not shown). In certain embodiments, any or all of the components or elements of optical system 400 may be enclosed within a housing or case 450, for example, to prevent or reduce the introduction of external or stray light, to protect optical system 400 from external dust and debris, and/or to shield from electrical or magnetic noise. In the illustrated embodiment of FIG. 23, light source 410 and optical sensor 420 are contained within housing 450. Alternatively, light source 410 and/or optical sensor 420 may be mounted on an external surface of housing 450 and/or may be partially located within housing 450.

In certain embodiments, optical system 400 is configured to provide simultaneous imaging of a large number reaction sites 104, 204 of article 100, 200, for example, a sufficiently large number of reaction sites 104, 204 to provide a dPCR analysis of one or more target molecules, sequence, genes, biological micro-organisms, or the like. For example, system 400 may be configured to simultaneously image at least 20,000 reaction sites 104, 204, wherein a density of reaction sites 104, 204 may be at least 100 reaction sites per square millimeter and/or each reaction site 104, 204 may have a characteristic diameter that is less than or equal to 100 micrometers. For example, an example embodiment of the instant invention (herein referred to as Example A), a two-dimensional array of 29,760 reaction sites 104, 204, each having a characteristic diameter of less than 70 micrometers, were simultaneously imaged and processed to provide a dPCR analysis of a target nucleotide sequence or molecule. In the Example A embodiment, reaction sites 104, 204 were arranged in a 160×186, hexagonally arrange pattern (like that shown in FIG. 6 or 13) over active area of an article 100, 200 that was less than 14 millimeters by about 14 millimeters (about 13 millimeters by about 13 millimeters). The reaction volume of each reaction site may be less than one nanoliter. In other embodiments, the active area of article 100, 200 comprises at least 15,000, at least 20,000 reaction sites 104, 204, at least 30,000 reaction sites 104, 204, at least 100,000 reaction sites 104, 204, or at least 1,000,000 reaction sites 104, 204.

Figure 24:
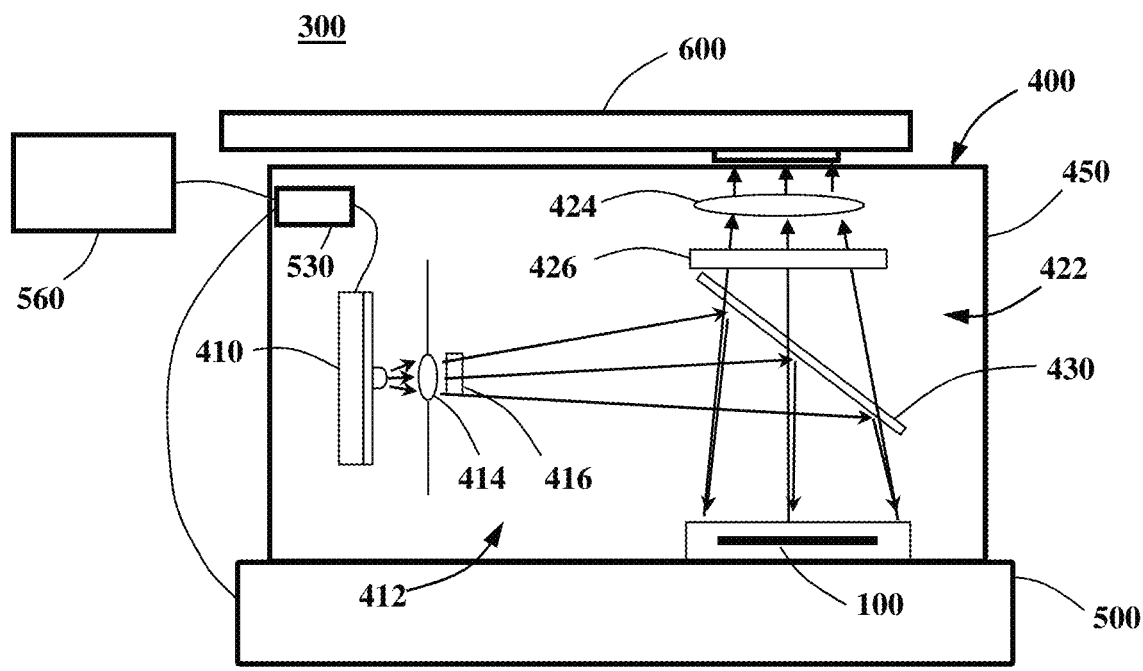
FIG. 24 is a schematic representation of system according to another embodiment of the present invention.

Referring to FIG. 24, an external photodetector, camera, or portable electronic device 600 may be mounted onto optical system 400 for obtaining optical images of article 100, 200 and/or associated optical signals or data from reaction sites 104, 204 of article 100, 200. Device 600 may be used in place of (e.g., FIG. 24), or in conjunction with (not shown), optical sensor 420. Device 600 may be removably mounted to optical system 400. For example, device 600 may be temporarily attached to optical system 400 to obtain images of article 100, 200 and/or reaction sites 104, 204 before, during, or after processing. Subsequent to obtaining one or more such images, device 600 may be detached for removed from optical system 400, for example, to view the images, transfer the images, and/or process the images (e.g., to enhance the images and/or obtain or calculate information related to biochemical reactions in one or more of the reaction sites 104, 204).

Device 600 may comprise an photodetector or optical sensor (e.g., a CCD or CMOS sensor) configured to receive one or more images of article 100, 200 and/or reaction sites 104, 204 when mounted to optical system 400. Device 600 may also include one or more lenses, filters, or other optical elements for providing images of article 100, 200 and/or reaction sites 104, 204. Len 424 may be configured to provide images on the photodetector of device 600. In certain embodiments, device 600 may include a lens or lens system (e.g., a camera lens including a system of lens elements). In such embodiments, the lens or lens system of device 600 may be configured to work with lens 424 of optical system 400 to provide images of a predetermined quality or characteristic. Alternatively, device 600 includes one or more lenses, or the like, for forming an image of article 100, 200 and/or reaction sites 104, 204, while optical system 400 contains no lenses such as lens 424 in the optical path between article 100, 200 and the photodetector of device 600.

In certain embodiments, device 600 is designed or configured specifically for use with optical system 400 for obtaining images of article 100, 200 and/or reaction sites 104, 204. Alternatively, device 600 may be configured for other uses besides obtaining images of article 100, 200 and/or reaction sites 104, 204. For example, device 600 may include a camera that may be configured for personal, commercial, and/or scientific photography. In certain embodiments, device 600 is a commercial or consumer device that may include uses apart from photographic applications. For example, device 600 may be a consumer or professional camera or video recorder, camera phone, smartphone (e.g., a mobile phone based on a mobile operating system including, but not limited to, Google's Android OS (operating system), APPLE ® iOS, NOKIA SYMBIAN ®, RIM's BLACKBERRY ® OS, SAMSUNG BADA ®, MICROSOFT WINDOWS ® Phone, HEWLETT-PACKARD® webOS, or an embedded LINUX® distributions such as Maemo and MeeGo, or other mobile phone built on a mobile computing platform), APPLE IPOD TOUCH® or similar device, personal digital assistant (PDA), portable media player, personal computer or electronic table with a photo input, or the like.

In certain embodiments, optical system 400 (e.g., the illustrated embodiments of FIGS. 23 and 24) is configured to be relatively small, while still providing an imaging quality of all of the reaction sites 104, 204 of article 100, 200 or nearly all of the reaction sites 104, 204 of article 100, 200 (e.g., at 90 percent, at least 95 percent, or at least 99 percent of the reaction sites 104, 204 of article 100, 200). For example, the size of optical system 400 may be configured to be sufficiently small so as to provide a compact system that is more readily portable that existing systems for conducting qPCR and/or dPCR tests, experiments, or analyses. Additionally or alternatively, the size of optical system 400 may be configured to be sufficiently small so as to maintain the cost of optical elements within a predetermined budget or target costs. For example, the focal length or effective focal length an imaging or camera lens, such as lens 424 shown in FIGS. 23 and 24 by be selected to provide a relatively short working distance. In such embodiments, a relatively sort focal length or effective focal length may also provide the ability to use relatively small lenses, beamsplitter(s), excitation filter(s), emission filters, and/or other systems components, thereby reducing overall material and/or system cost of goods.

Importantly, it has been discovered that decreasing the size of optical system 400 (e.g., the illustrated embodiments of FIGS. 23 and 24) and/or a decreasing a characteristic imaging system focal length or effective focal length, for example as compared to prior art PCR systems used for similar purposes, may be restricted by design or system constraints to maintain reaction site 104, 204 image quality at or above a predetermined amount. For example, optical aberrations such as astigmatism, distortion and field curvature have been found to decrease image quality, particularly of images of peripheral reaction sites in a two-dimensional array of reaction sites 104, 204, by an amount that may preclude obtaining a desired accuracy in dPCR calculations used to determine the number count of one or more target nucleotide sequences or molecules. Surprisingly, it has been discovered that the use of certain design methodologies and/or optical figures of merit may result in systems and instruments that produce sufficient image quality of an array of reaction sites 104, 204 to allow detection and/or quantification of target nucleotide sequences or molecules in a sample, for example, through the use of amplification processes such as qPCR and/or dPCR.

In certain embodiments, emission optical system or imaging system 422 is configured according to a design method to provide a miniaturized optical system for detecting and/or quantifying target nucleotide sequences or molecules contained in at least some of reaction sites 104, 204. The design of emission optical system 422 may be complicated by the existence of various components that interact in a non-linear way. The design of emission optical system 422 may also be complicated when limited to only a finite number of commercially available components, for example, where cost constraints preclude or reduce the use of custom optics. Miniaturized optical elements available from certain consumer market driven applications, such cell phone and smartphone cameras, may be utilized in the current design method to provide very low component prices. For example, the specification and characteristics of commercially available hardware and optic elements produced for these markets is finite and may not match desired or preferred values for use in the development of a miniaturized instruments to identify and/or quantify target nucleotide sequences or molecules.

In certain embodiments, the current design method may use a scanning microscope approach to provide systems and instruments according to embodiments of the present invention. Alternatively, design method may use a camera design approach to provide systems and instruments according to embodiments of the present invention. The camera design method may consist of an object, a photographic lens or objective, and a pixilated sensor such as a CCD or CMOS sensor. In the case of camera design methods, an entire field of regard (FOR) may be sensed at once over a time interval herein referred to as an "exposure time".

The design method may include incorporation of an optical "object". Without limiting the scope of embodiments of the present invention, the object may comprise a well array plate, which may consist of as many as 96 or 384 individual wells in an 80×120 mm gridded format. The wells may be spaced at a 9 millimeter or 4.5 millimeter pitch. Alternatively, smaller numbers of wells spaced at these pitches may also be used. In certain embodiments, the object may be a substrate with an array of through-holes that are 350 microns in diameter and spaced 500 microns apart. The through-holes may be gridded into 8×8 sub grids arranged in a 4×12 pattern. Additionally or alternatively, the object used in the current design method may comprise one or more of configurations of article 100, 200 discussed above herein.

The design method may include the use of a commercially available photographic objective lens, since by design such lenses image a wide FOR with low aberrations. These lenses may be multi-element (at least 3 lens elements, up to as many as 11 or more lens elements). The limiting aperture (aperture stop) may be inside the lens assembly and controls a "speed" or f/# (light gathering power) of the lens, where f/# may be defined as the ratio of a lens or system focal length divided by the diameter of the limiting aperture. This lens design type is very mature and a large number of choices have been specifically designed various type of commercially available sensors (e.g., CCD and CMOS sensors). These sensors convert light energy into electrical energy and typically consist of millions of individual sensing elements, each element receiving energy imaged through the photographic objective lens from a small part of the FOR. The electrical signals from each of these sensing elements (called picture elements, or "pixels") is assembled through software that allow a 2-dimensional representation of the object imaged by the objective.

Embodiments of the design method will now be describe in greater detail in which the optical object comprises article 100, 200 described above as the Example A embodiment. A CMOS sensor may be used in embodiments of the current design method, due to the relatively low cost of these sensors compared to CCD sensors providing similar performance, for example, in terms of pixel resolution, frame rate, and/or dynamic range. It will be appreciated that in other embodiments of the design method, a CCD or other type of photodetector may be utilized.

In certain embodiments, hole or spot finding algorithms and quantifying algorithms may provide that an image of each reaction site 104, 204 comprise at least 5 pixels across a hole diameter or about 20 pixels total. For the present embodiment, a value of about 8 pixels across a well or hole diameter is selected. For the Example A embodiment of article 100, 200, the holes are characterized by a diameter of 60 micrometers and are arranged in a hexagonal pattern in which adjacent reaction sites 104, 204 are spaced at a pitch of 82 micrometers. Since 8 pixels span 60 microns and they are spaced at an 82 micron pitch, the hole spacing is 11 pixels, leaving approximately 3 dark pixels between adjacent reaction sites 104, 204. Along one axis of the CMOS detector, there are about 160 reaction site images on a side, which provide a CMOS pixel design parameter of about 1760 pixels on a side, or a total number of detector pixels of at least about 3.1 million for a square active area of article 100, 200. In certain embodiments, an even large number of sensor pixels may be selected to accommodate for positioning consideration and/or increased lens aberrations at the edges of the FOR.

The next consideration in the current design method may be pixel size. Currently available sensors have, for example, 1.1, 1.4, 2.2, 3, 5, 8, 11 micrometers and larger square pixel sizes. There are three factors which may influence choice of pixel size: dynamic range (DR), signal to noise ratio, and diffraction. DR may be determined by the maximum number of photoelectrons which can be stored by each pixel. The absolute number for 2.2 micrometer diameter pixels is about 3200 photoelectrons and about 20,000 photoelectrons for 5.5 micron pixels. As a general design parameter, larger pixels (greater number of photoelectrons) provide better DR, as well as better signal to noise ratio (SNR) characteristic, which is equal to the square root of the signal. A 20K DR has an SNR of 140; a 3.2K DR has an SNR of 57, which is 2.5× less.

Diffraction is a fundamental characteristic of electromagnetic waves in general and light waves in particular. It is caused by truncation of the wave's extent by a physical aperture such as a lens or system aperture stop. The effect in an optical system is that the image of a perfect point source infinitely far away (such as a star) is not itself infinitely small, but is a blob whose exact shape is determined by the size and shape of the aperture. The circular aperture of a most lenses create a bulls-eye type pattern with a bright, large central ring (the so called "Airy disk") and infinite number of smaller and less bright surrounding circles. For the visible wavelengths, the size of the Airy disk is approximately equal to the f/# of the system objective lens in microns. Thus, diffraction considerations move an optical design toward larger lens diameters and system apertures. However, there is a practical limitation on the lens diameter or aperture, since lens aberrations (such as, but not limited to, astigmatism, distortion and field curvature) caused by the surface shapes of the lens elements increase as the f/# decreases or lens diameter increases. A practical value for f/# is about f/2.5. This means that the image of a point source will create a circular image of about 2.5 microns diameter. If a pixel is 2.5 microns square, the Airy Disk will just fit inside. If the pixel is 1.4 microns, then the Airy disk will occupy a 2×2 pixel grid. One evaluation criteria for calculating a lens or system resolution is called the Rayleigh criterion, which states that two point objects are just resolved by an optical system when the image the maximum of one Airy disk occurs at the minimum of the other. This would imply that two adjacent pixels in the current example should be separated by one Airy disk radius, or about 1.25 microns. Another resolution evaluation criteria is to separate adjacent signals by at least one Airy disk diameter. This latter criteria provides a limit of the size of the pixel to 2.5 microns square or larger. The overall size of a sensor with this pixel size and pixel count becomes 1760×2.5=4400 microns or 4.4 mm.

Two commercially available sensors meeting the above criteria for the current design method are the Aptina MT9P031 monochrome CMOS sensor (4.28 millimeters× 5.7 millimeters and 1944×2592 pixels having a diameter of 2.2 micrometers by 2.2 micrometers) and the DX sized 16 Mp sensor of the Nikon D7000 camera (23.6×15.6 millimeters and 5 micrometer by 5 micrometer pixels). In the current example, the Aptina MT9P031 may be selected based on cost considerations.

Based on the smaller diameter of the Aptina CMOS sensor of 4.28 millimeters and an active area of 13 millimeters by 13 millimeters for article 100, 200 in the Example A embodiment, the system magnification is 0.33 (4.28/13). This provides a reaction sites 104, 204 image size of 60 micrometers×0.33=19.8 microns. Thus, each reaction site 104, 204 image covers 19.8/2.5=7.92 pixels, which meets both criterion above of greater than 5 pixels and of about 8 pixels.

The current design method further comprises determining the accuracy of intensity calculations based on signals received from reaction sites 104, 204 when emission optical system 422 is used to image article 100, 200 onto photodetector 420. In the current example, the intensity calculation is based on an image size of each reaction site that is about 5 sensor pixels in diameter. The effectiveness of an optical detection system such as emission optical system 422 is dependent on the signal to noise ratio (SNR). For fluorescence sensing instruments one rule of thumb is that the SNR be at least 3. The place where the SNR is measured is at the sensor transducer. This transducer transforms optical energy (photons) to electrical energy (electrons). These electrons are usually called "photoelectrons"—literally electrons produced by photons. SNR may comprise two parts: signal energy and noise energy. Signal energy (signal photoelectrons) results from photon flux (photon arrival rate, photons/second). Noise energy may be produced by several mechanisms, such as the signal itself, optical background energy (from sources other than the signal source), and transducer-related energy such as read noise or dark (thermal) noise. A more detailed discussion of read and dark noise is found in U.S. Pat. Nos. 7,233,393 and 7,045,756, which are herein incorporated by reference in their entirety.

When an accurate estimate of the noise energy is determined or provided, SNR calculations may be used to determine if a given signal energy is large enough to overcome the noise energy. Transducers (optical detectors) may be characterized for read noise and for thermal noise. The signal flux at the detector can be estimated from detector quantum efficiency (QE), optical throughput (the ratio of photons measured to the ratio of photons generated at the sample, for example), and the optical flux produced at the optical source (laser, LED, lamp, arc, etc . . . ). Optical throughput may be composed of source spectral flux, optical filter spectral transmission characteristics, fluorescence conversion efficiency (proportion of incident flux at a wavelength 1 that gets converted to fluorescence emitted flux at a wavelength 2, angular extent of the emitted optical flux, optical gathering efficiency of camera lens, and other characteristics of windows, fluids and any other materials in the optical path. Optical background can be calculated by knowledge of the throughput characteristics of the optical components and the residual transmission of the optical filters at normally blocked wavelengths, (auto) fluorescence of materials in the optical path, and scattered light produced within the confines of the structure containing the optical system. Background may be difficult to model, but may be obtained from measurements in the system.

Based on the current design method, the imaging system comprises the Aptina CMOS sensor and a system magnification of 0.33. Using a general design criteria that the system be small, various commercially available objective lenses designed for surveillance systems and cell phones were evaluated in light of the design criteria that the imaging system provide a predetermined intensity calculation accuracy for all, or nearly all, reaction sites 104, 204. These lenses have the added advantage of being relatively inexpensive. It was determined from this evaluation that the Sunex lens model number DSL901 produced total aberrations that were low enough to meet the predetermined intensity calculation accuracy criteria. The DSL901 is an f/3 lens and has focal length of 15 millimeters, which results in a working distance of 60 millimeters, using the relationship, $p=f[(m+1)/m]$, where f=focal length
p=working distance.

As alternatives, other photographic objectives were identified that meet the predetermined intensity calculation accuracy criteria. These photographic objective have focal lengths that are less than or equal to the 15 millimeter focal length of the DSL901. In certain embodiments, the magnification may be slightly less than 0.33. This will result in a slightly larger system, due to an increase in working distance; however, the lower magnification advantageously reduces aberrations such as astigmatism, which are larger at peripherally located reaction sites 104, 204 within the FOR.

In summary, it has been discovered that a system including an optical imaging system having a working distance that is less than or equal to 60 millimeters may be provided that is able to receive an article 100, 200 comprising at least 20,000 separate reaction sites 104, 204, simultaneously illuminate the at least 20,000 separate reaction sites 104, 204, and calculate a number of target nucleotide particles contained in some or all of the at least 20,000 separate reaction sites. In certain embodiments, an accurate calculation of the number target nucleotide particles is obtained by providing a photodetector, such as photodetector 420, comprising a predetermined number of pixels that is at least 20 times the number of separate reaction sites. In other embodiments, the predetermined number of pixels is at least 60 times the number of separate reaction sites or at least 100 times the number of separate reaction sites.

In certain embodiments, an imaging system according to embodiments of the design method discussed above may be characterized by one or more figures of merit (FOM). Some FOMs include:

Sensor pixel square size>=camera lens f# (e.g., for systems with wavelengths in the visible part of the spectrum).

Number of sensor pixels>=(n*n*1*w)/(p*p), where n=required pixels/feature in image, l=object field of regard length, w=object field of regard width, p=feature pitch.

Choose magnification to be the smallest of the four ratios of sensor length/width to object length/width.

Choose lens focal length and object to image distance pairs (determined by magnification) to provide best compromise between lens aberrations and overall optics package length.

In certain embodiments, system 300 further comprises a thermal control system 500 comprising, for example, a thermal cycler configured to perform a PCR procedure or protocol on some or all of the samples contained in article 100, 200. Systems 400, 500 may combined or coupled together into a single unit, for example, in order to perform a qPCR and/or a dPCR procedure, assay, experiment, or protocol on at least some of the samples contained in article 100, 200. In such embodiments, computer 530, 560 may be used to control systems 400, 500 and/or to collect or process data provided or obtained by either or both systems 400, 500. Alternatively, thermal control system 500 may be completely separate from optical system 400 and/or from computer 530, 560. In such embodiments, optical system 400 may be used to perform a dPCR or end-point PCR procedure on the samples contained in reaction sites 104, 204 after thermal cycle has been performed on the samples using thermal control system 500 or some other thermal controller or thermal cycler. In certain embodiments, thermal control system 500 comprises a thermal cycler in which PCR is done using a traditional thermal cycler, isothermal amplification, thermal convention, infrared mediated thermal cycling, or helicase dependent amplification. In certain embodiments, at least a portion of thermal control system 500 may be integrated with or into article 100, 200. For example, article 100, 200 may include one or more heating elements distributed along one or both surfaces 110, 112. Additionally or alternatively, at least portions of substrate 102 may be a heating element, for example, by being made of a material with an electrical resistance configured to provide resistive heating upon application of a voltage potential to substrate 102.

According to various embodiments, emission optical system 422 and/or lens 424 may comprise a focal length that is less than or equal to 15 mm and/or a working distance that is less then or equal to 60 mm, where the working distance of the distance from articles 100, 200 to lens 424 or a principal plane of lens 424. Furthermore, in various embodiments, emission optical system 422 and/or lens 424 comprise an f-number that is less than or equal to 3. In some embodiments, emission optical system 422 and/or lens 424 may comprise both a focal length that is less than or equal to 15 mm and an f-number that is less than or equal to 3.

In certain embodiments, article 100, 200 comprises an electronic chip comprising integrated circuits and semiconductor. In such embodiment, a detection system may also be integrated into the chip to determine the presence and/or quantity of a biological components of interest.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

Exemplary systems for methods related to the various embodiments described in this document include those described in following U.S. provisional patent applications:

U.S. provisional application number 61/612,087, filed on Mar. 16, 2012; and

U.S. provisional application number 61/723,759, filed on Nov. 7, 2012; and

U.S. provisional application number 61/612,005, filed on Mar. 16, 2012; and

U.S. provisional application number 61/612,008, filed on Mar. 16, 2012; and

U.S. provisional application number 61/723,658, filed on Nov. 7, 2012; and

U.S. provisional application number 61/723,738, filed on Nov. 7, 2012; and

U.S. provisional application number 61/659,029, filed on Jun. 13, 2012; and

U.S. provisional application number 61/723,710, filed on Nov. 7, 2012; and

U.S. provisional application number 61/774,499, filed on Mar. 7, 2013; and

Life Technologies Docket Number LT00655 PCT, filed Mar. 15, 2013; and

Life Technologies Docket Number LT00656 PCT, filed Mar. 15, 2013; and

Life Technologies Docket Number LT00657 PCT, filed Mar. 15, 2013; and

Life Technologies Docket Number LT00658 PCT, filed Mar. 15, 2013; and

Life Technologies Docket Number LT00668 PCT, filed Mar. 15, 2013.

All of these applications are also incorporated herein in their entirety by reference.

What is claimed is:

1. A system for determining the number of target nucleotide molecules in a sample using digital polymerase chain reaction (dPCR), the system comprising:
   an article comprising at least 20,000 separate reaction sites distributed over an active area of 13 millimeters by 13 millimeters or greater;
   a carrier configured to house the article;
   an excitation optical system comprising a light source configured to simultaneously illuminate the at least 20,000 separate reaction sites;
   an optical sensor comprising a predetermined number of pixels, wherein the predetermined number of pixels is at least 60 times the number of reaction sites, and wherein the optical sensor provides an image of at least five pixels across a diameter of each reaction site; and
   an emission optical system configured to have a magnification of at most 0.33, wherein the emission optical system is configured to include a lens having a focal length such that a working distance from the carrier is less than or equal to 60 millimeters, wherein the lens and the optical sensor are configured to produce images of the at least 20,000 separate sites that meet an intensity calculation accuracy, wherein the intensity calculation accuracy is selected based on dynamic range, a signal-to-noise ratio equal to a square root of a dynamic range, and diffraction.

2. The system of claim 1, further comprising a computer including a processor and an electronic memory in communication with the processor, wherein:
   the computer receives images from the optical sensor of the at least 20,000 separate reaction sites;
   the memory comprises instructions for performing a digital PCR calculation; and
   the computer is configured to calculate, based on the instructions and received images, a number of target nucleotide particles contained in at least some of the at least 20,000 separate reaction sites.

3. The system of claim 1, further comprising:
   a housing containing the excitation optical system and the emission optical system; and
   an image recording system comprising the optical sensor, wherein the image recording system is detachably mounted to the housing.

4. The system of claim 3, wherein the image recording system is a camera phone or a smartphone.

5. The system of claim 3, wherein the image recording system comprises a processor configured to acquire images from the optical sensor and to process the images to provide biochemical information of the sample.

6. The system of claim 1, further comprising a beamsplitter configured to reflect excitation light from the excitation optical system to the sample and to transmit emission light from the sample to the optical sensor.

7. The system of claim 1, wherein each of the reaction sites has a diameter of 50 micrometers to 75 micrometers.

8. The system of claim 1, wherein the signal-to-noise ratio is at least 3.

* * * * *

UNITED STATES PATENT AND TRADEMARK OFFICE
CERTIFICATE OF CORRECTION

| | | |
|---|---|---|
| PATENT NO. | : 11,987,840 B2 | Page 1 of 1 |
| APPLICATION NO. | : 16/234287 | |
| DATED | : May 21, 2024 | |
| INVENTOR(S) | : Kevin Maher | |

It is certified that error appears in the above-identified patent and that said Letters Patent is hereby corrected as shown below:

On the Title Page

In Column 1, item (73), under Assignee, Line 1, delete "Technologi s" and insert -- Technologies --, therefor.

Signed and Sealed this
Twenty-first Day of January, 2025

Coke Morgan Stewart
*Acting Director of the United States Patent and Trademark Office*